(12) United States Patent
Andrade et al.

(10) Patent No.: US 12,042,750 B2
(45) Date of Patent: Jul. 23, 2024

(54) PROCESS AND SYSTEM FOR HEAT INTEGRATION IN ETHANOL PRODUCTION

(71) Applicant: Whitefox Technologies Limited, London (GB)

(72) Inventors: Virginia Andrade, Calgary (CA); Jin Ming Zhou, Calgary (CA); Stephan Rüdiger Blum, Calgary (CA)

(73) Assignee: WHITEFOX TECHNOLOGIES LIMITED, London (GB)

( * ) Notice: Subject to any disclaimer, the term of this patent is extended or adjusted under 35 U.S.C. 154(b) by 0 days.

(21) Appl. No.: 17/897,853

(22) Filed: Aug. 29, 2022

(65) Prior Publication Data

US 2022/0410028 A1    Dec. 29, 2022

Related U.S. Application Data

(63) Continuation of application No. 16/983,460, filed on Aug. 3, 2020, now Pat. No. 11,426,675, which is a (Continued)

(51) Int. Cl.
*B01D 3/00* (2006.01)
*B01D 3/14* (2006.01)
(Continued)

(52) U.S. Cl.
CPC ............ *B01D 3/007* (2013.01); *B01D 3/143* (2013.01); *B01D 53/04* (2013.01); *C07C 29/76* (2013.01);
(Continued)

(58) Field of Classification Search
CPC ........ B01D 3/007; B01D 3/143; B01D 53/04; C07C 29/76; C07C 29/80
See application file for complete search history.

(56) References Cited

U.S. PATENT DOCUMENTS

| 4,217,178 A | 8/1980 | Katzen et al. |
| 4,306,942 A | 12/1981 | Brush |

(Continued)

FOREIGN PATENT DOCUMENTS

| JP | 2016047530 | 4/2016 |
| WO | 2016088134 | 6/2016 |

OTHER PUBLICATIONS

Roy, Christian; "Vaperma Siftek Membrane for Ethanol Refining: A General Presentation"; Vaperma, Inc.; Mar. 2010; (32 pages).

(Continued)

*Primary Examiner* — Deborah D Carr
(74) *Attorney, Agent, or Firm* — K&L Gates LLP

(57) ABSTRACT

The present disclosure provides processes and systems for heat integration in ethanol production. In one embodiment, a feed mixture is distilled with one or more distillation units to remove at least a portion of the water, and form a distillation unit bottom stream, a vaporous overhead stream, and a fusel oil stream. Molecular sieve units are regenerated by vacuum or a combination of vacuum and optionally a portion of the product stream to form one or more regenerate streams. A feed tank is configured to receive at least one selected from a condensed portion of the regenerate streams and a portion of a vaporous depressure stream, to form a feed stream. The energy contained in the depressure vapor is recovered by the depressure vapor contacting the feed tank and heating up at least one stream forwarded into the feed tank.

15 Claims, 36 Drawing Sheets

Related U.S. Application Data continuation of application No. 15/836,558, filed on Dec. 8, 2017, now Pat. No. 10,729,987.

(60) Provisional application No. 62/552,817, filed on Aug. 31, 2017, provisional application No. 62/522,394, filed on Jun. 20, 2017, provisional application No. 62/432,008, filed on Dec. 9, 2016.

(51) Int. Cl.
*B01D 53/04* (2006.01)
*C07C 29/76* (2006.01)
*C07C 29/80* (2006.01)

(52) U.S. Cl.
CPC ........ *C07C 29/80* (2013.01); *B01D 2253/108* (2013.01); *B01D 2256/24* (2013.01); *B01D 2257/80* (2013.01); *B01D 2259/40083* (2013.01)

(56) References Cited

U.S. PATENT DOCUMENTS

| | | | |
|---|---|---|---|
| 4,326,036 A | 4/1982 | Hayes | |
| 4,340,446 A | 7/1982 | Crawford | |
| 4,405,409 A | 9/1983 | Tusel et al. | |
| 4,407,662 A | 10/1983 | Ginder | |
| 4,422,903 A | 12/1983 | Messick | |
| 4,428,799 A | 1/1984 | Standiford | |
| 4,978,430 A | 12/1990 | Nakagawa et al. | |
| 5,105,029 A | 4/1992 | Ninomiya et al. | |
| 5,124,004 A | 6/1992 | Grethlein et al. | |
| 7,470,348 B2 | 12/2008 | Seiki et al. | |
| 7,572,353 B1 | 8/2009 | Vander Griend | |
| 7,594,981 B2 | 9/2009 | Ikeda | |
| 7,699,961 B2 | 4/2010 | Ikeda et al. | |
| 7,732,173 B2 | 6/2010 | Mairal et al. | |
| 7,744,727 B2 | 6/2010 | Blum et al. | |
| 7,867,365 B2 | 1/2011 | Brown | |
| 7,922,872 B2 | 4/2011 | Kihara et al. | |
| 8,103,385 B2 | 1/2012 | Macharia | |
| 8,128,787 B2 | 3/2012 | Wynn et al. | |
| 8,128,826 B2 | 3/2012 | Plante et al. | |
| 8,129,573 B2 | 3/2012 | Kikuchi et al. | |
| 8,142,662 B2 | 3/2012 | Osora et al. | |
| 8,425,734 B2 | 4/2013 | Goel et al. | |
| 8,585,904 B2 | 11/2013 | Osora et al. | |
| 8,858,798 B2 | 10/2014 | Osora et al. | |
| 9,149,769 B2 | 10/2015 | Seiki et al. | |
| 9,194,623 B2 | 11/2015 | Kihara et al. | |
| 9,925,476 B2 | 3/2018 | Crawford et al. | |
| 10,118,107 B1 | 11/2018 | Kwik et al. | |
| 10,729,987 B1* | 8/2020 | Andrade | C07C 29/80 |
| 11,426,675 B2* | 8/2022 | Andrade | B01D 3/42 |
| 2007/0000769 A1 | 1/2007 | Brown | |
| 2007/0131533 A1 | 6/2007 | Blum et al. | |
| 2008/0135396 A1 | 6/2008 | Blum | |
| 2008/0207959 A1* | 8/2008 | Plante | B01D 3/14 568/916 |
| 2009/0004713 A1 | 1/2009 | Wynn | |
| 2009/0057128 A1 | 3/2009 | Vane et al. | |
| 2009/0117631 A1 | 5/2009 | Cote et al. | |
| 2009/0215139 A1 | 8/2009 | Datta et al. | |
| 2009/0301970 A1* | 12/2009 | Noel | B01D 3/145 210/640 |
| 2010/0051441 A1 | 3/2010 | Vane et al. | |
| 2010/0219128 A1 | 9/2010 | Seiki et al. | |
| 2010/0314320 A1 | 12/2010 | Osora et al. | |
| 2011/0108409 A1 | 5/2011 | Brown | |
| 2011/0130598 A1 | 6/2011 | Huang et al. | |
| 2011/0315541 A1 | 12/2011 | Xu | |
| 2012/0137727 A1 | 6/2012 | Huang | |
| 2013/0165678 A1 | 6/2013 | Kohl | |
| 2015/0087041 A1* | 3/2015 | Parten | C12P 7/10 435/165 |
| 2016/0107964 A1 | 4/2016 | Matsukata et al. | |
| 2016/0324205 A1 | 11/2016 | Herbst | |
| 2017/0203230 A1 | 7/2017 | Raiser | |
| 2017/0204030 A1 | 7/2017 | Maeda et al. | |

OTHER PUBLICATIONS

Gabardo, Helio "Dehydration of Ethanol via Membrane Polymeric Siftek", Dec. 4, 2009 (34 pages).
Search Report and Written Opinion issued for International PCT Application No. PCT/IB2019/000546 filed on May 7, 2019.

\* cited by examiner

PROCESS AND SYSTEM FOR HEAT INTEGRATION IN ETHANOL PRODUCTION

REFERENCE TO PENDING PRIOR PATENT APPLICATIONS

This patent application is a continuation of U.S. patent application Ser. No. 16/983,460, filed on Aug. 3, 2020, which is a continuation of U.S. patent application Ser. No. 15/836,558, filed on Dec. 8, 2017, which is incorporated herein by reference in its entirely and claims the benefit of U.S. Provisional Patent Application No. 62/432,008, filed on Dec. 9, 2016, U.S. Provisional Patent Application No. 62/522,394, filed on Jun. 20, 2017, and U.S. Provisional Patent Application No. 62/552,817, filed on Aug. 31, 2017, the entire contents of each of which are hereby incorporated herein by reference.

BACKGROUND

Various processes and systems have been used for producing ethanol from feedstock. For example, in some prior systems, ethanol is produced by fermentation, yielding a stillage (beer) with an ethanol concentration of up to 18%, which is subsequently concentrated in three steps: (1) distillation in a beer column, increasing the ethanol concentration up to 65%, followed by (2) processing in a stripper/rectifier column further increasing the ethanol concentration to around 90 vol %, and (3) a molecular-sieve-based dehydration (also referred to as pressure swing adsorption) to a target ethanol concentration of 99.0 to 99.95 vol %.

In the stripper/rectifier column, a mixture of high boiling components including propanol, butanol, and isomeric pentanols (also referred to as fusel oil) may need to be removed in a side draw to avoid accumulation therein. In some prior systems, pressurized product vapor coming from the molecular sieve unit (MSU) is acidic mainly due to carbonic acid, and the pressurized product vapor may need to be de-acidified in an acid removal column (ARC). As pressure decreases and temperature increases, carbonic acid dissociates into $CO_2$ (a non-condensable gas) and water. The ARC is a counter-current vapor/liquid adsorption/desorption unit with vapor entering the bottom of the column flowing upward and liquid entering the top of the column flowing downward. Through the counter-current flow, the vapor condenses and heats up the liquid, thus driving out the $CO_2$ gas.

SUMMARY

According to one non-limiting aspect of the present disclosure, an example embodiment of a method of integrating heat in ethanol production is described. The example method includes distilling a feed mixture including ethanol and water with one or more distillation units to remove at least a portion of the water, and to form a distillation unit bottom stream, a vaporous overhead stream, and a fusel oil stream. A plurality of molecular sieve units are contacted with a byproduct stream including at least one selected from a portion of the vaporous overhead stream and at least a portion of the fusel oil stream, thereby forming a product stream and one or more regenerate streams. At least one of the plurality of molecular sieve units is regenerated by vacuum or a combination of vacuum and optionally a portion of the product stream to form one or more regenerate streams. At least a portion of the regenerate streams is condensed. At least one selected from a condensed portion of the regenerate streams, a portion of the fusel oil stream, and a portion of a vaporous depressure stream is forwarded to a feed tank, to form a feed stream. The feed stream is contacted with a separation system, thereby forming a permeate, a retentate, and a stripper bottom stream. Heat is exchanged between at least a portion of the depressure stream and at least one selected from (1) at least a portion of scrubber water streams, (2) at least a portion of the fusel oil stream, (3) at least the condensed portion of the regenerate streams, and (4) at least a portion of the permeate.

According to another non-limiting aspect of the present disclosure, an example embodiment of a system for heat integration in ethanol production is described. The system includes one or more distillation units configured to receive a feed mixture including ethanol and water, to remove at least a portion of the water, and to form a distillation unit bottom stream, a vaporous overhead stream, and a fusel oil stream. A plurality of molecular sieve units are configured to contact a byproduct stream including at least one selected from a portion of the vaporous overhead stream and at least a portion of the fusel oil stream. The plurality of molecular sieve units are configured to form a product stream and one or more regenerate streams. The plurality of molecular sieve units are configured to be regenerated by vacuum and optionally a portion of the product stream to form one or more regenerate streams. A feed tank is configured to receive a condensed portion of the regenerate streams and a vaporous depressure stream, to form a feed stream. A separation system is configured to contact the feed stream, thereby forming a permeate, a retentate, and a stripper bottom stream.

In certain non-limiting embodiments of the system, the system includes a scrubbing system forming a scrubber water stream comprising ethanol. A line is in fluid communication with the feed tank to forward at least a portion of the scrubber water stream into the feed tank.

BRIEF DESCRIPTION OF THE DRAWINGS

Features and advantages of the processes and systems described herein may be better understood by reference to the accompanying drawings in which.

Figure 1:
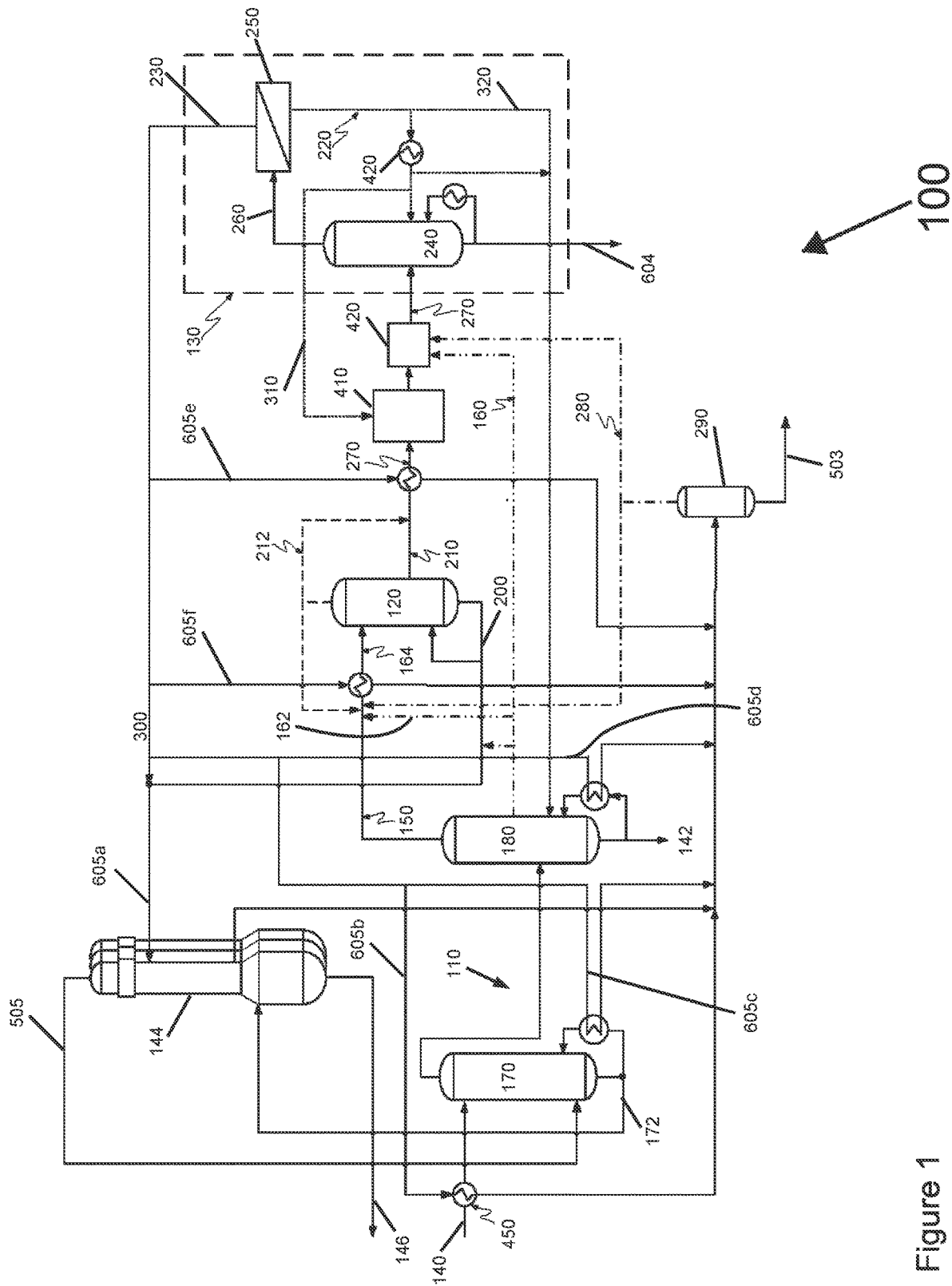
FIG. 1 is a schematic illustration of a non-limiting example embodiment of a system for heat integration in ethanol production according to the present disclosure.

The reader will appreciate the foregoing details, as well as others, upon considering the following detailed description of certain non-limiting embodiments of processes and systems according to the present disclosure. The reader may also comprehend certain of such additional details upon using the processes and systems described herein.

DETAILED DESCRIPTION

Prior systems for producing ethanol from feedstock typically require molecular sieve units (MSUs) for dehydrating the feed vapor coming from the stripper/rectifier column or a dedicated vaporizer. The MSUs include two or more beds filled with zeolite pellets, which adsorb water to produce anhydrous vapor until they are saturated with water. While the first bed undergoes a regeneration cycle, the feed vapor coming from the stripper/rectifier column can be switched to a second bed for continued dehydration. The saturated zeolite bed can be regenerated by vacuum or a combination of vacuum and sweep (a portion of the product stream) to form one or more regenerate streams. Due to the water desorption, a first regenerate stream (also referred to as MSU Regen) has an ethanol concentration between 50 and 80 vol %, and a second regenerate stream (also referred to as Depressure) between 80 vol % and 99 vol %. Both need to be recycled upstream for reprocessing. This operation has a number of disadvantages. For example, as a large portion of ethanol is continuously recycled, (1) capacity in the upstream distillation is used up for dehydrating the MSU Regen, (2) capacity in the rectifier overheads condenser is used up to condense the Depressure stream, (3) capacity in the MSU itself is used up to essentially dehydrate its own regenerate streams for recycling, and (4) additional energy or steam and cooling water are required for the reprocessing of the MSU Regen and the Depressure streams. Thus, there has developed a need for processes and systems that overcome the limitations of the process for dehydrating a byproduct stream in ethanol production.

The present disclosure, in part, is directed to processes and systems for dehydrating a byproduct stream in ethanol production. A feed mixture including ethanol and water is distilled with one or more distillation units to remove at least a portion of the water, and form a distillation unit bottom stream, a vaporous overhead stream, and a fusel oil stream. At least a portion of the fusel oil stream can be combined with the vaporous overhead stream, thereby producing a first byproduct stream. The first byproduct stream is contacted with a molecular sieve unit, thereby forming a product stream. At least one of the molecular sieve units is regenerated by vacuum and optionally a portion of the product stream to form one or more regenerate streams. A second byproduct stream including at least one of (1) a portion of the regenerate streams and (2) a portion of the fusel oil stream is contacted with a separation system, thereby forming a permeate and a retentate.

In certain non-limiting embodiments of the method, heat is exchanged between at least a portion of the retentate and the feed mixture. In certain non-limiting embodiments of the method, heat is exchanged between the at least a portion of the retentate and the distillation unit bottom stream. In certain non-limiting embodiments of the method, heat is exchanged between at least a portion of the retentate and the first byproduct stream. In certain non-limiting embodiments of the method, heat is exchanged between at least a portion of the retentate and a portion of the regenerate streams.

In certain non-limiting embodiments of the method, heat is exchanged between at least a portion of the stripper unit bottom stream and at least one selected from the group consisting of the feed mixture, the distillation unit bottom streams, the first byproduct stream, and a portion of the regenerate streams. In certain non-limiting embodiments of the method, heat is exchanged between at least a portion of the regenerate streams and at least one selected from the feed mixture, the distillation unit bottom streams, the first byproduct stream, a feed condensation system, and the second byproduct stream.

Referring to FIG. 1, the illustrated embodiment of the system or production plant 100 for dehydrating a byproduct stream in ethanol production includes a plurality of distillation units 110, an MSU 120, and a separation system 130. The plurality of distillation units 110 are configured to receive a feed mixture 140 including ethanol and water, to remove at least a portion of the water, and form a distillation unit bottom stream 142, vaporous overhead stream 150, and a fusel oil stream 160. A "fusel oil" as used herein includes definitions that are generally known in the chemical engineering art, and can refer to a mixture of high boiling components including propanol, butanol, and isomeric pentanols.

In certain non-limiting embodiments, the distillation unit 110 includes one or more beer columns 170 and a stripper/rectifier column 180. In the beer column 170, the feed mixture 140 is distilled, increasing the ethanol concentration up to 65%. Subsequently, in the stripper/rectifier column 180 the ethanol concentration is further increased to around 90 vol %. In certain non-limiting embodiments, the beer column 170 forms a beer column stillage stream 172, and heat is exchanged between the beer column stillage stream 172 and the retentate 605c, as further explained below. Although FIG. 1 illustrates the system 100 as including two distillation units 170, 180, in other embodiments, the system 100 may include a single distillation unit or may include three or more distillations units.

In certain non-limiting embodiments, the distillation units 110 are in fluid communication with one or more evaporators 144, which form an evaporator stillage stream 146. For example, the system 100 can include two or more, three or more, four or more, five or more, six or more, seven or more, or eight or more evaporators 144. The process and system described herein are not limited in this regard. As further explained below, heat can be exchanged in the evaporators 144 between the beer column stillage stream 172 and at least one selected from the MSU product steam and the retentate (which are condensed). The beer column stillage stream 172 can have a solids content of approximately 7%. By exchanging heat between the beer column stillage stream 172 and the MSU product stream 200 and/or retentate 300, some of the water in the beer column stillage stream 172 can be evaporated, which can increase the solids content to become a thick stillage as the stillage travels through the evaporators 144, forming the evaporator stillage stream 146 with a solids content of approximately 35%.

In certain non-limiting embodiments, at least a portion of the fusel oil stream 160 (e.g., the vaporous portion of the fusel oil stream 162) can be combined with the vaporous overhead stream 150, thereby producing a first byproduct stream 164. In certain non-limiting embodiments, the at least a portion of the condensed overhead stream 150 and at least a portion of the liquid fusel oils are vaporized to form the first byproduct stream 164. In certain non-limiting embodiments, the first byproduct stream 164 includes only the vaporous overhead stream 150 and not the fusel oil stream 160. In other embodiments, the fusel oil stream 160 may be blended into the first byproduct stream 164. The MSU 120 includes one ore more beds, and is configured to contact the first byproduct stream 164 to form a product stream 200.

With continuing reference to FIG. 1, the MSU 120 is regenerated by vacuum and optionally a portion of the product stream to form the MSU regenerate streams 210 (MSU Regen), 212 (Depressure). Although FIG. 1 illustrates the MSU 120 as forming two MSU regenerate streams 210, 212, in other embodiments the MSU 120 can form a single stream. In some embodiments, the first MSU regenerate stream 210 is a water-rich stream (e.g., having approximately 50% water and approximately 50% ethanol), and the second MSU regenerate stream 212 is a water-lean stream (e.g., having approximately 3% water and approximately 97% ethanol). The regeneration of the MSU 120 is a discontinuous desorption process, gradually removing the water by applying by vacuum and optionally a portion of the product stream. There are both high pressure and low pressure molecular sieve systems; the regeneration of each involves use of a relative vacuum in the regeneration step. Referring to FIG. 1, in the illustrated embodiment at least a portion of the second MSU regenerate stream 212 is forwarded into the first byproduct stream 164. In another embodiment, all of the second MSU regenerate stream 212 can be forwarded in a direction away from the MSU 120. In one embodiment the second MSU regenerate stream 212 is directed to tank 420 where the energy available in regenerate stream 212 can be recovered.

In certain non-limiting embodiments, the separation system 130 is configured to contact a second byproduct stream 270 including at least one of (1) the MSU regenerate streams 210, 212, and (2) at least a portion of the fuel oil stream 160, thereby forming a permeate 220, a retentate 230, and a stripper bottom stream 604. In certain non-limiting embodiments, at least a portion of the retentate 230 can be forwarded into the product stream 200 via a retentate line 300. In certain non-limiting embodiments, at least a first portion of the permeate 220 is forwarded into the separation system 130 via a first permeate line 310, and at least a second portion of the permeate 220 is forwarded into at least one of the distillation units 170, 180 via a second permeate line 320. In some embodiments, the first portion of the permeate 220 is condensed before being forwarded into the separation system 130. In some embodiments, the first portion of the permeate 220 is condensed and combined with the second byproduct stream 270 before being forwarded into the separation system 130. In some embodiments, the second portion of the permeate 220 is condensed before being forwarded to at least one of the distillation units 110. In some embodiments, the second portion of the permeate 220 is forwarded into at least one of the distillation units 110 via the second permeate line 320 (direct vapor injection). In some embodiments, all permeate 220 may be forwarded to the separation system 130. In other embodiments, all permeate 220 may be forwarded into at least one of the distillation units 110. In certain non-limiting embodiments, re-injecting the permeate 220 as a vapor into the distillation units 110 can recuperate its latent heat there.

In certain non-limiting embodiments, the second byproduct stream 270 includes at least a portion of the fuel oil stream 160. In some embodiments, the second byproduct stream 270 is blended with at least a portion of an overhead vent stream 280 before being contacted with the separation system 130. For example, a flash tank 290 is in fluid communication with the MSU 120, and forms the overhead vent stream 280. A "vent stream" as used herein includes definitions that are generally known in the chemical engineering art, and can refer to a flash recycle stream resulting from the condensation of an MSU product. In certain non-limiting embodiments, at least portion of the overhead vent stream 280 is forwarded into the first byproduct stream 164. In certain non-limiting embodiments, at least portion of the overhead vent stream 280 is forwarded into the separation system via tank 420 where the energy available in vent stream 280 can be recovered.

In certain non-limiting embodiments, the separation system 130 includes a stripper/vaporizer unit 240 and a membrane 250. The stripper/vaporizer unit 240 is configured to receive at least one of (1) the fuel oil stream 160 and (2) the MSU regenerate streams 210, 212 and form a membrane feed vapor 260, and the membrane 250 is configured to contact the membrane feed vapor 260, thereby forming the permeate 220 and the retentate 230. In certain non-limiting embodiments, the stripper/vaporizer unit 240 is a stripper unit; in other embodiments, the stripper/vaporizer unit 240 is a vaporizer unit. A stripper unit forms a pure water bottom stream, whereas a vaporizer unit forms only enriched ethanol vapors substantially without any bottom stream. In certain non-limiting embodiments, the permeate 220 is forwarded into the stripper unit 240 of the separation system 130 either as a liquid (shown) or a vapor (not shown).

In certain non-limiting embodiments, the separation system 130 is pressurized (e.g., to at least 0.3 MPa or 1 MPa), thereby heating the retentate 230. In other embodiments, the separation system 130 can be operated at a low pressure (e.g., vacuum). The heat contained in the vaporous retentate 230 is recuperated in an upstream heat exchanger (e.g., MSU superheater) 605e to reduce the overall energy consumption of the entire distillation/dehydration section of the plant 100, as further explained below.

In certain non-limiting embodiments, the membrane 250 is a polymer membrane built on a hollow fiber backbone. In certain non-limiting embodiments, a selective layer is placed on either the outside (shell side) or inside (lumen side) of the hollow fibers. In other embodiments, the membrane 250 may assume any other form, for example including zeolites as adsorbents, so long as the membrane 250 can dehydrate the membrane feed vapor 260 to certain water contents depending on the usage requirements or preferences for the particular plant 100.

In certain non-limiting embodiments, the second byproduct stream 270 defines an azeotropic ethanol concentration. An "azeotropic mixture" as used herein includes definitions that are generally known in the chemical art, and can refer to a mixture of two or more liquids in such a way that its components cannot be altered by simple distillation. In certain non-limiting embodiments, the retentate 230 has an ethanol concentration higher than the azeotropic ethanol concentration.

In certain non-limiting embodiments, the separation system 130 can be pre-assembled as a unit. In this way, the separation system 130 can be installed to new systems 100 at final assembly, or retrofitted to existing plants that use extractive distillation with such separation systems. In certain non-limiting embodiments, the separation system 130 is integrated without additional power (e.g., electricity) requirement, and the retentate 230 is discharged by pressure without any power supply.

The main benefits of the dedicated separation system 130 are that it (1) frees up capacity in the main distillation and/or the rectifier overheads condenser, (2) reduces load to the MSU, and (3) significantly reduces the overall energy and cooling water consumption of the distillation/dehydration section. Another benefit of the dedicated separation system 130 is that the freed-up capacity in the distillation units 110 and the MSU 120 can be used to increase overall production capacity, as the amount of the ethanol that was previously recycled as MSU regenerate streams can be supplied through the beer column 170. For example, the capacity of the plant 100 can be increased up to 30% without size changes to the stripper/rectifier column 180 or the MSU 120 and without increasing energy consumption on a per-gallon basis. Depending on the usage requirements or preferences for the particular plant 100, the separation system 130 can avoid the recirculation of the MSU regenerate streams 210, 212 into the stripper/rectifier column 180, rendering the distillation units 110 less prone to fluctuations and allowing a more efficient operation.

In certain non-limiting embodiments, the energy contained in the retentate 230 can be recuperated in the plant 100. Put another way, the plant 100 can provide upstream heat integration. In certain non-limiting embodiments, heat is exchanged between at least a portion of the retentate 230 and at least one selected from the feed mixture 140, the distillation unit bottom stream 142, the first byproduct stream 164, the beer column stillage stream 172, and a portion of the MSU regenerate streams 210, 212. In certain non-limiting embodiments, the heat exchange can be achieved via tie-ins of lines or a heat recovery unit configured to receive at least a portion of the retentate 230 and at least one selected from the feed mixture 140, the distillation unit bottom stream 142, the first byproduct stream 164, the beer column stillage stream 172, and a portion of the MSU regenerate streams 210, 212. The result of this heat integration is that energy savings in the main process are larger than the additional energy consumption of the separation system 130 (e.g., 30% or more), thereby reducing the overall energy and cooling water consumption of the plant 100 on a per-gallon basis in a compact footprint.

Referring to FIGS. 2-5, in the illustrated embodiments a scrubbing system 105 is used to remove ethanol from vent gases (e.g., $CO_2$, with traces of ethanol). There are vents in various sections of the plant (e.g. fermenter, distillation columns). These vent streams contain non-condensable gases ($CO_2$), ethanol, water and low boiling components (e.g. aldehydes). Vent streams are directed to a gas/liquid adsorption system (scrubber system) which can consist of multiple scrubber columns) where the vent streams flow upward and are contacted in counter current operation with liquid water raining downward. In certain non-limiting embodiments, the ethanol is absorbed in the water and is removed at the bottom of the scrubber and recycled back as a dilute stream with an ethanol concentration of approximately 1.5 vol % into the plant. The ethanol free non-condensable gases and some low boiling components (aldehydes) are being removed at top of the scrubber and released elsewhere (e.g. atmosphere of $CO_2$ recovery system). In other embodiments, a separate scrubber treatment system may treat at least a portion of the dilute scrubber water to produce a concentrated scrubber water stream with an ethanol concentration of 8-12 vol %. In certain non-limiting embodiments, at least a portion of (1) the concentrated scrubber water stream and/or (2) the dilute scrubber water can be sent to the feed tank 420. Also, at least a portion of (1) the concentrated scrubber water stream and/or (2) the dilute scrubber water 107 can be used as cold streams for heat integration.

In the illustrated embodiment, at least a portion of the product stream 200P is forwarded to a flash vessel 290, thereby forming a vent stream 503. A second byproduct stream 270 including at least one of (1) a portion of the regenerate streams 210a (MSU Regen), 210b (MSU Regen), 307 (Depressure), (2) a portion of the first byproduct stream 164a and 164b, (3) a portion of the fusel oil stream 160a and 160b, (4) a portion 503a, 503 of the vent stream and (5) a portion of the scrubber water stream 107 (dilute 1.5 vol % or concentrated 8-12% scrubber water to feed tank) is contacted with the separation system 240, 250, and 420, thereby forming the permeate 220, the retentate 230, and a stripper unit bottom stream 604. In certain non-limiting embodiments of the method, heat is exchanged between a portion of the retentate 605b and the feed mixture to the beer column. In another embodiment, heat is exchanged between at least a portion of the retentate 605c, 605d, 605g and the distillation unit bottom streams. In another embodiment, heat is exchanged between at least a portion of the retentate 605f and the first byproduct stream. In another embodiment, heat is exchanged between a portion of the retentate 605a and evaporators 144. In another embodiment, heat is exchanged between at least a portion of the retentate 605e and at least a portion of the second byproduct stream 270. In another embodiment, heat and material is exchanged between at least a portion of the retentate 605h and the molecular sieve 120.

Figure 2:
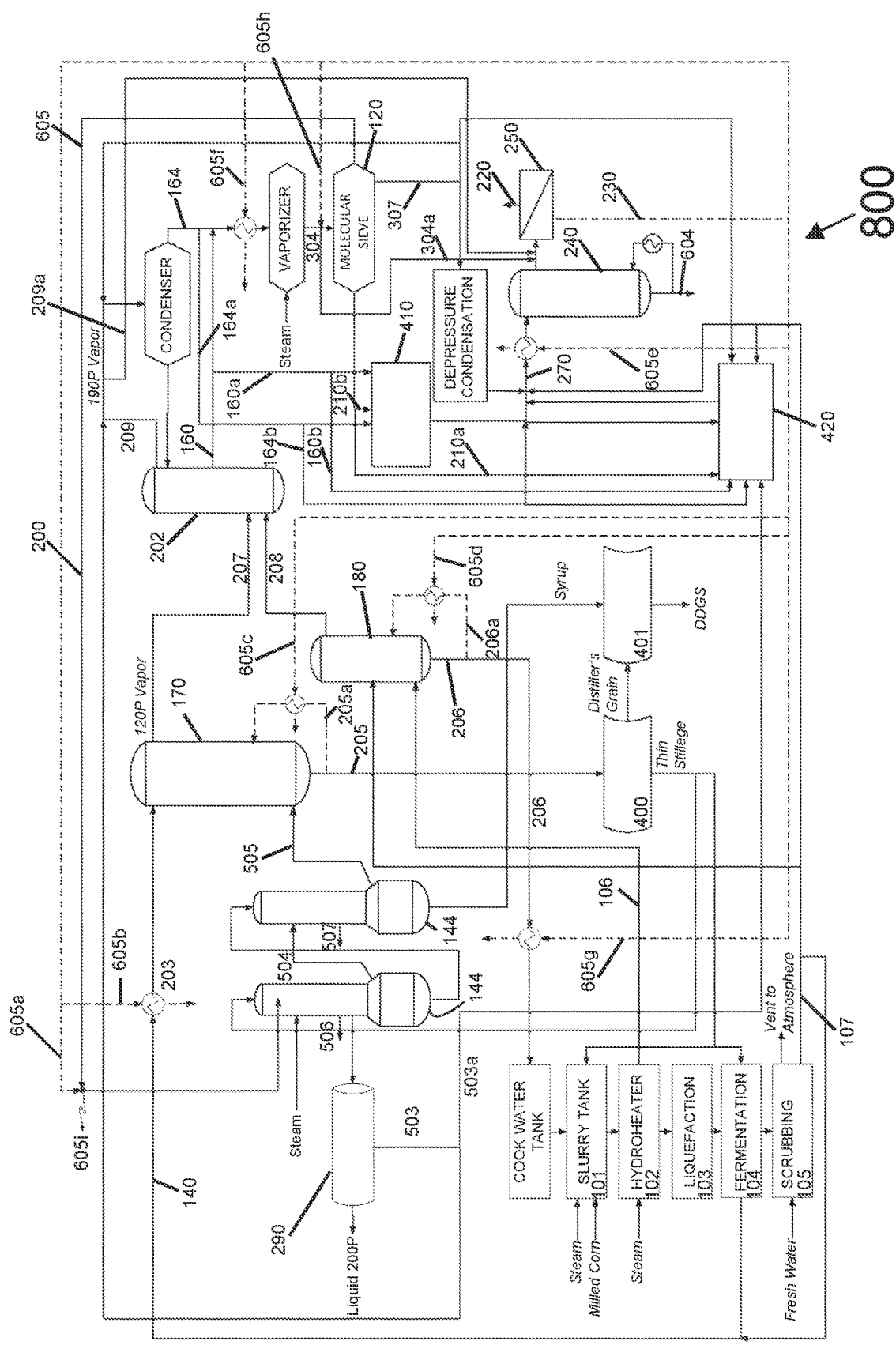
FIG. 2 is a schematic illustration of another non-limiting example embodiment of a system for heat integration in ethanol production according to the present disclosure.

With continuing reference to FIG. 2, in the illustrated embodiment steam generated in at least one of (1) evaporators 505, (2) a hydroheater 106, and (3) a boiler is injected to the distillation units as energy source for their operation. The steam injected in the distillation units increases the water content and dilutes the solids contained in the distillation unit bottom streams. The solids in distillation unit bottom streams are recovered in at least one selected from a centrifuge 400, a dryer 401, and the evaporators 144. In certain non-limiting embodiments of the method, at least a portion of the steam injected on the distillation units is replaced by reboiling at least one selected from a portion of the beer column stillage stream 205 and the stripper-rectifier bottom stream 206. A benefit of the reboilers is that energy savings can be up to 30%, and the capacity of the plant 800 can be increased up to 30% without size changes to the stripper/rectifier column and without increasing energy consumption on a per-gallon basis.

In certain non-limiting embodiments of the method, heat and material is exchanged by directing the vaporized overhead vapor 304a into the feed 220 to membrane. In certain non-limiting embodiments of the method, heat and material is exchanged by directing the rectifier overhead vapor 209a into the feed 220 to membrane.

Figure 3:
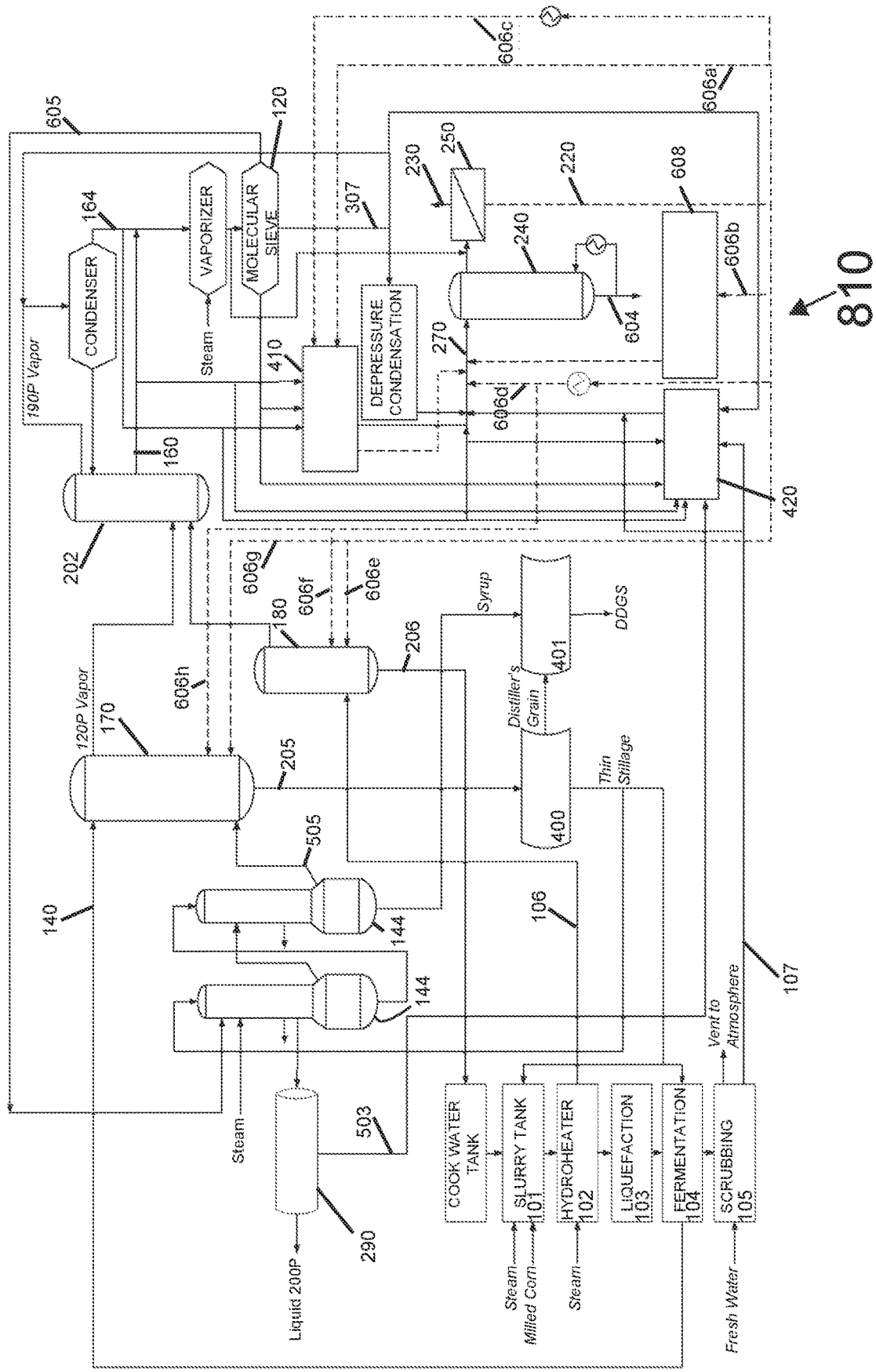
FIG. 3 is a schematic illustration of yet another non-limiting example embodiment of a system for heat integration in ethanol production according to the present disclosure.

Referring to FIG. 3, in the illustrated embodiment the vapor permeate 220 can be integrated into the second byproduct stream. In certain non-limiting embodiments of the method, at least a portion of the permeate 606a is forwarded into the second byproduct stream 270 via the regenerate condensation vacuum system 410. In another embodiment, at least a portion of the permeate 606b is forwarded into the second byproduct stream 270 via the permeate condensation vacuum system 608. The permeate condensation vacuum system is designed to condense the vapor permeate and to generate the vacuum required by the membrane unit 250 in the separation system. In another embodiment, a portion of the permeate 606d is forwarded into the second byproduct stream 270 via direct contact. In another embodiment, at least a portion of the permeate 606e, 606f, 606g, 606h is forwarded into the second byproduct stream via the distillation units. In certain non-limiting embodiments of the method, at least a portion of the permeate 606c is forwarded into the second byproduct stream 270 via the regenerate condensation vacuum system 410 after being condensed in a separate heat exchanger.

Figure 4:
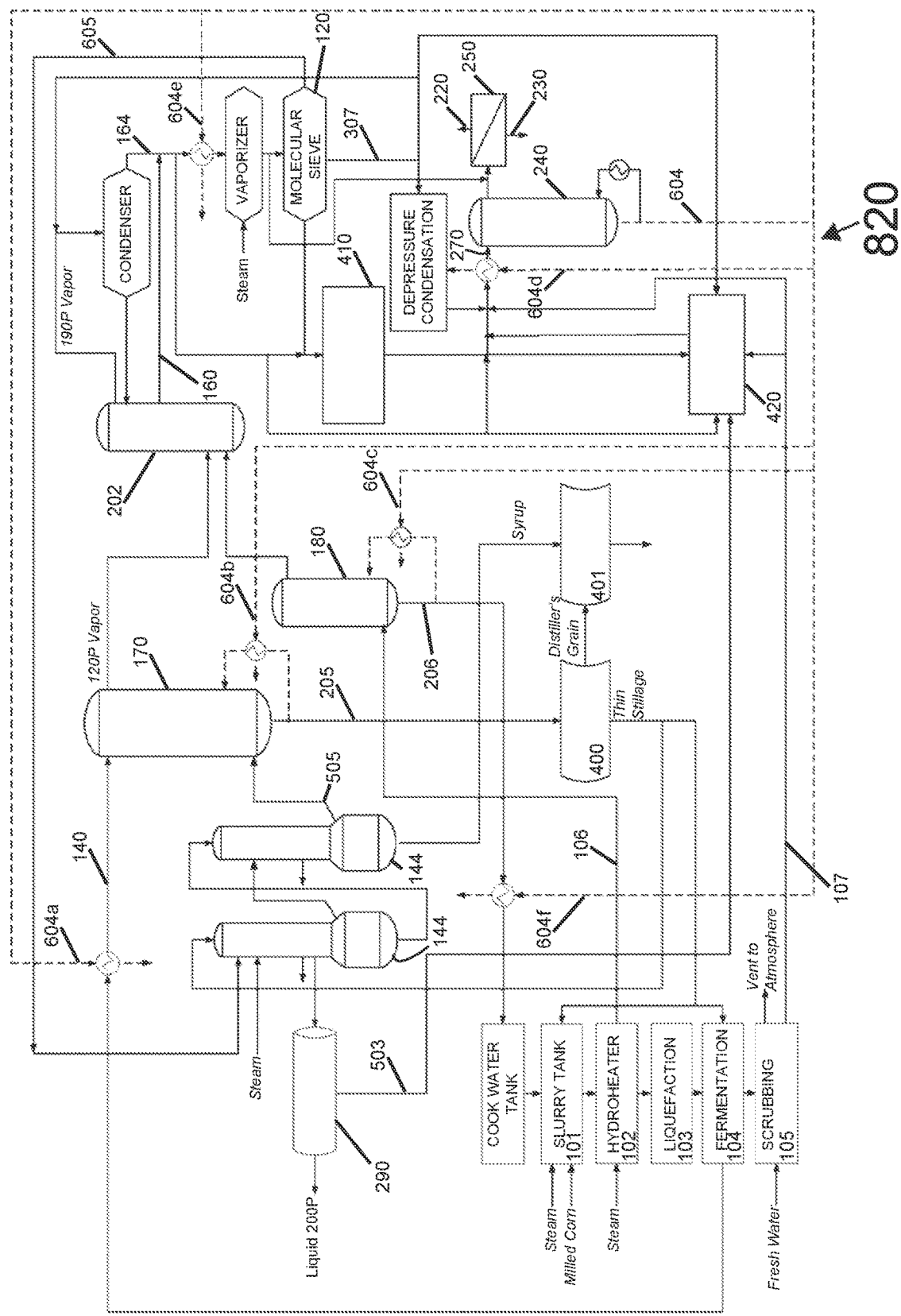
FIG. 4 is a schematic illustration of yet another non-limiting example embodiment of a system for heat integration in ethanol production according to the present disclosure.

Referring to FIG. 4, in the illustrated embodiment the plant 820 can provide heat integration from the stripper unit bottom stream. In certain non-limiting embodiments of the method, heat is exchanged between at least a portion of the stripper unit bottom stream 604a and the feed mixture. In another embodiment, heat is exchanged between a portion of the stripper unit bottom stream 604b, 604c, and 604f and the distillation unit bottom streams. In another embodiment, heat is exchanged between at least a portion of the stripper unit bottom stream 604e and the first byproduct stream. In another embodiment, heat is exchanged between a portion of the stripper unit bottom stream 604d and at least a portion of the second byproduct stream 270.

Figure 5:
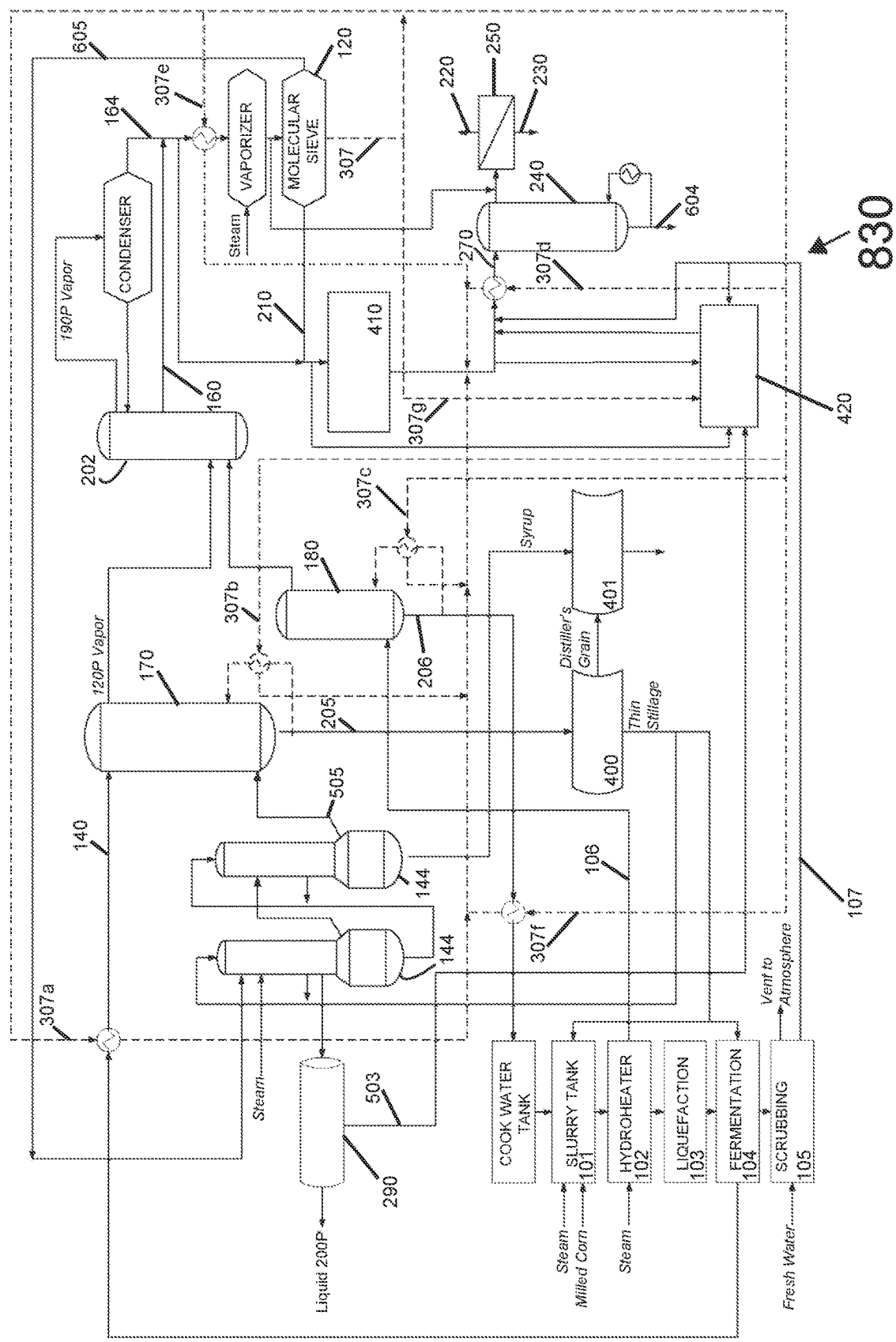
FIG. 5 is a schematic illustration of yet another non-limiting example embodiment of a system for heat integration in ethanol production according to the present disclosure.

Referring to FIG. 5, in the illustrated embodiment the plant 830 can provide heat integration from at least one of the regenerate streams (also referred to as depressure stream). In certain non-limiting embodiments of the method, heat is exchanged between a portion of the depressure stream 307a and the feed mixture. In another embodiment, heat is exchanged between a portion of the depressure stream 307b, 307c, and 307f and the distillation unit bottom streams. In another embodiment, heat is exchanged between at least a portion of the depressure stream 307e and the first byproduct stream. In another embodiment, heat is exchanged between a portion of the depressure stream 307g and a feed tank 420 which is designed to recover the energy available in vaporous streams including the depressure stream. In another embodiment, heat is exchanged between a portion of the depressure stream and the second byproduct stream 270 via heat exchangers 307d.

Figure 6:
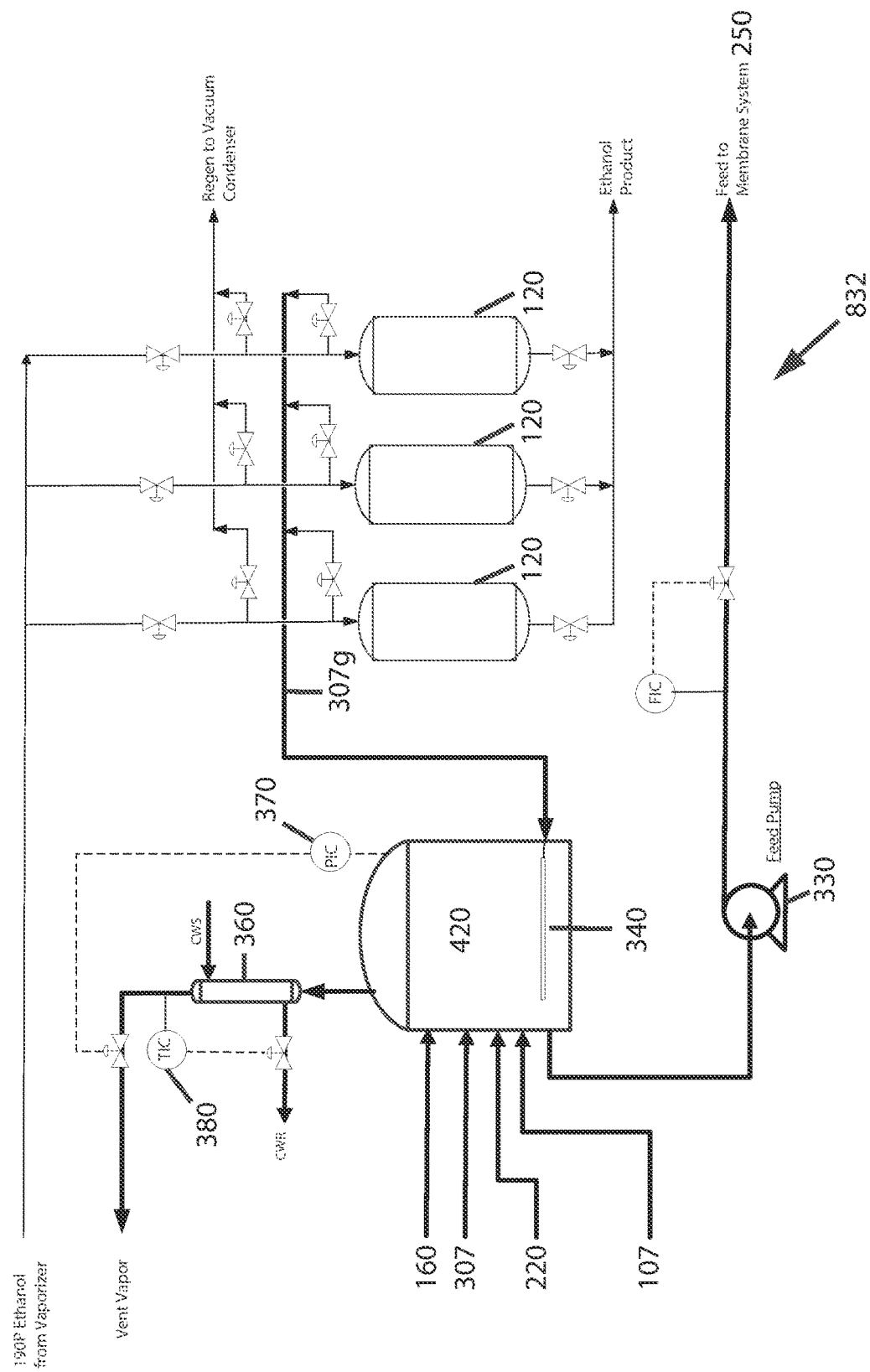
FIG. 6 is a schematic illustration of yet another non-limiting example embodiment of a system for heat integration in ethanol production according to the present disclosure.

Referring to FIG. 6, in the illustrated embodiment the plant 832 includes three MSUs 120 which undergo rotating tasks to complete a full cycle of absorbing/depressure/vacuum generation process: one bed is under an absorbing process, one bed is under a depressure process, and one bed is under a regenerate removal process. In certain non-limiting embodiments, at least one of the MSUs 120 is regenerated by vacuum and optionally a portion of the product stream to form one or more regenerate streams. In this manner, high-purity ethanol can be obtained from an active MSU, while a passive MSU is being regenerated. In certain embodiments, the MSUs may be cyclically regenerated in sequence, from the first MSU to the second MSU, and the third MSU, and then again the first MSU, the second MSU, and the third MSU. In other embodiments, the MSUs may be regenerated in other manners, for example, from the first MSU to the second MSU, and the third MSU, and then in reversed order, to the second MSU, and the first MSU. In further embodiments, a particular MSU may not be regenerated in a given cycle. For example, the MSUs may be regenerated in a sequence from the first MSU to the third MSU, then again to the first MSU, and the second MSU, and again the first MSU. The methods and systems described herein are not limited in this regard.

In certain non-limiting embodiments, the energy contained in the depressure vapor from the MSUs 120 is recovered by the depressure vapor contacting the feed tank 420 and heating up at least a portion of the regenerate stream 307 and the permeate 220. In some prior systems for producing ethanol from feedstock, during the depressure step, the hot ethanol/water with an ethanol concentration of around 90% wt. is released from the pressured MSU bed (e.g., 70-80 psia) and injected into the rectifier overheads 190-proof ethanol vapor condenser, which operates under a vacuum of approximately 6-10 psia to be condensed by cooling water. The combined condensate of the rectifier overheads and the depressure stream is partly sent back to the rectifier top as reflux and partly as 190-proof ethanol vapor to the 190-proof ethanol vapor storage tank. The depressure condensation occurs as a sudden burst (e.g., 20-40 sec) of vapor being condensed in the 190-proof ethanol condenser. This step is typically repeated every 3-6 minutes for the other MSU beds.

One drawback in some prior systems is that the depressure stream may form a permanent recycle stream for the MSU as it is condensed in the 190-proof ethanol vapor condenser, pumped to the 190-proof ethanol vapor storage tank, and then pumped again from storage to a pressurized vaporizer, which produces vaporous feed to the MSU. A second drawback is that the depressure heat energy is wasted, since the hot vapor is condensed directly by cooling water, especially as significant heat must be rejected to cooling water in a very short time. A third drawback is that rectifier operation is affected by the intermittent depressure stream and cannot maintain a stable operation. A fourth drawback is that the sudden, cyclical condensation in the 190-proof ethanol vapor condenser poses a mechanical challenge, exerting stress on the welding seams.

With continuing reference to FIG. 6, in the illustrated embodiment a feed tank 420 is added to buffer the feed flow of the regenerate stream 307 and the permeate 220 before they are sent to the membrane system 250 by a feed pump 330. The depressure hot vapor 307g from MSU beds 120 is redirected to the feed tank 420 through a heat recovery unit 340. In certain non-limiting embodiments, the heat recovery unit 340 comprises a set of spargers or a perforated steam ring 340 located on the bottom of the feed tank 420. In other embodiments, however, the heat recovery unit 340 can assume a variety of shapes or designs. In the feed tank 420, the depressure vapor 307g contacts at least a portion of the cold regenerate stream 307 and the permeate 220, and gets condensed while the cold regenerate stream 307 and the permeate 220 are heated up by the depressure hot vapor 307g. A vapor condenser 360 is located on the top of the tank 420 in order to condense any remaining vapor escaped from the tank 420. Depending on the usage requirements or preferences for the particular plant 832, a pressure control loop 370 and a temperature control loop 380 can be added to minimize vent flow and maximize the heat recovery. Dilute and/or concentrated scrubber water 107 from $CO_2$ scrubber system 105 also can be added to the feed tank 420 to increase the overall heat recovery. Fusel oil draw (FOD) 160 also can be added to this tank 420 to eliminate the FOD 160 influence on the MSU 120 operation.

The main benefits of the illustrated embodiment are (1) elimination of the depressure recycle, (2) heat recovery of energy contained in the depressure stream 307g, (3) reduction of cooling water requirements in the 190-proof ethanol condenser, (4) elimination of mechanical stress on the 190-proof ethanol condenser, and (5) elimination of pressure fluctuations in the rectifier (particularly relevant in combination of also treating the regenerate stream 307 through the membrane system 250). Another benefit of the illustrated embodiment is that the vapor 307g can be condensed in numerous ways including condensers that are generally known in the chemical engineering art and by selecting a variety of cold streams, including, but not limited to, scrubber water 107, Fusel Oil Draw (FOD) 160, the regenerate stream 307, and the permeate 220. Another benefit of the tank 420 is that the heat recovery of sudden bursts can be eliminated. In this regard, the tank 420 acts as a surge capacitor buffer for the depressure vapor 307g.

Figure 7:
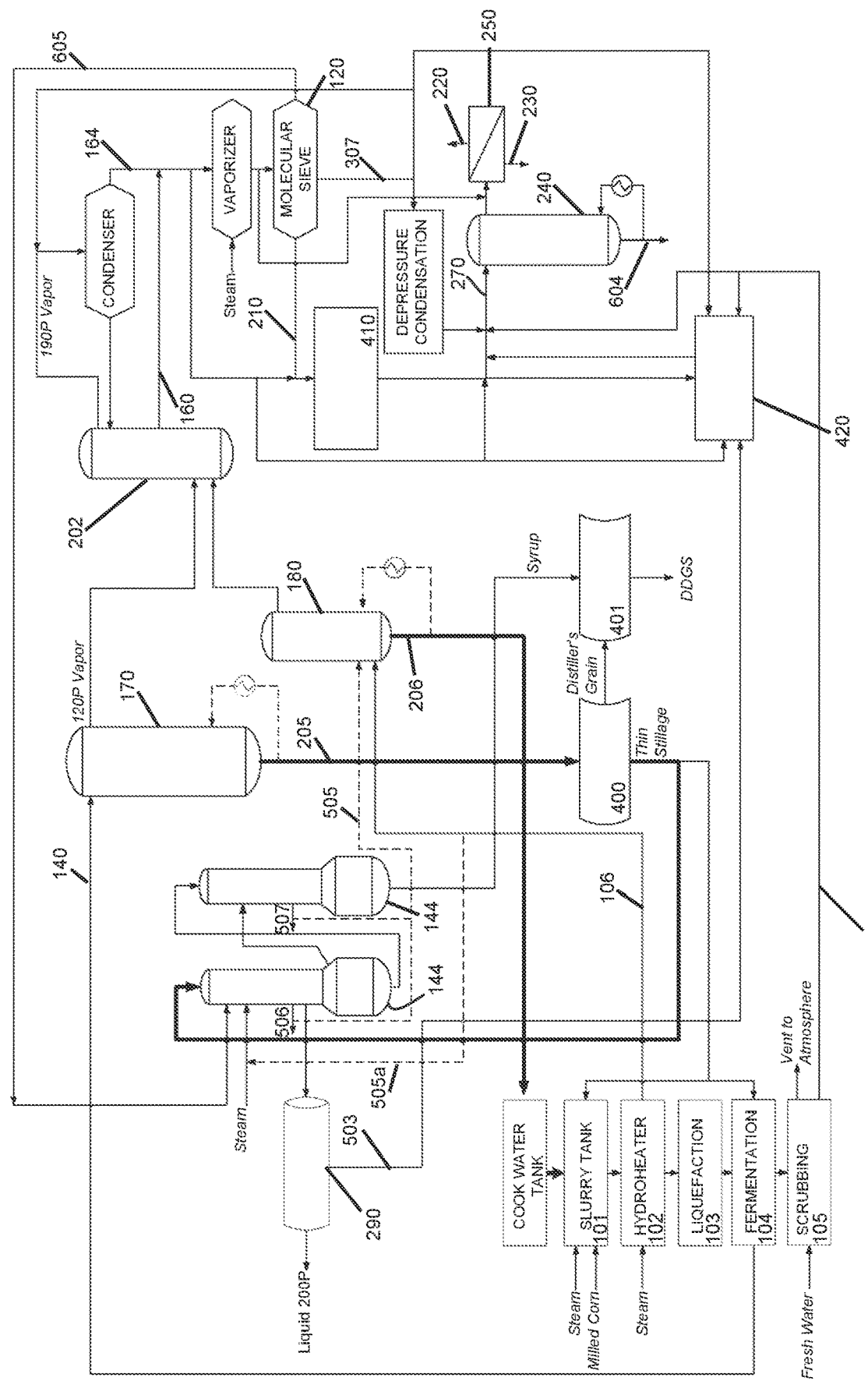
FIG. 7 is a schematic illustration of yet another non-limiting example embodiment of a system for heat integration in ethanol production according to the present disclosure.

Referring to FIG. 7, in the illustrated embodiment the energy displaced in the distillation units by forwarding at least a portion of the regenerate streams into the second byproduct stream allows to forward (1) at least a portion of the steam 505a from the hydroheater into the evaporators, and (2) steam 505 from the evaporators to the distillation unit. A benefit of this energy re-balancing of the plant 100 is that energy savings may be 30% or higher, and the capacity of the plant 100 may be increased 30% or higher without size changes to the stripper/rectifier column and without increasing energy consumption of a per-gallon basis.

Figure 8:
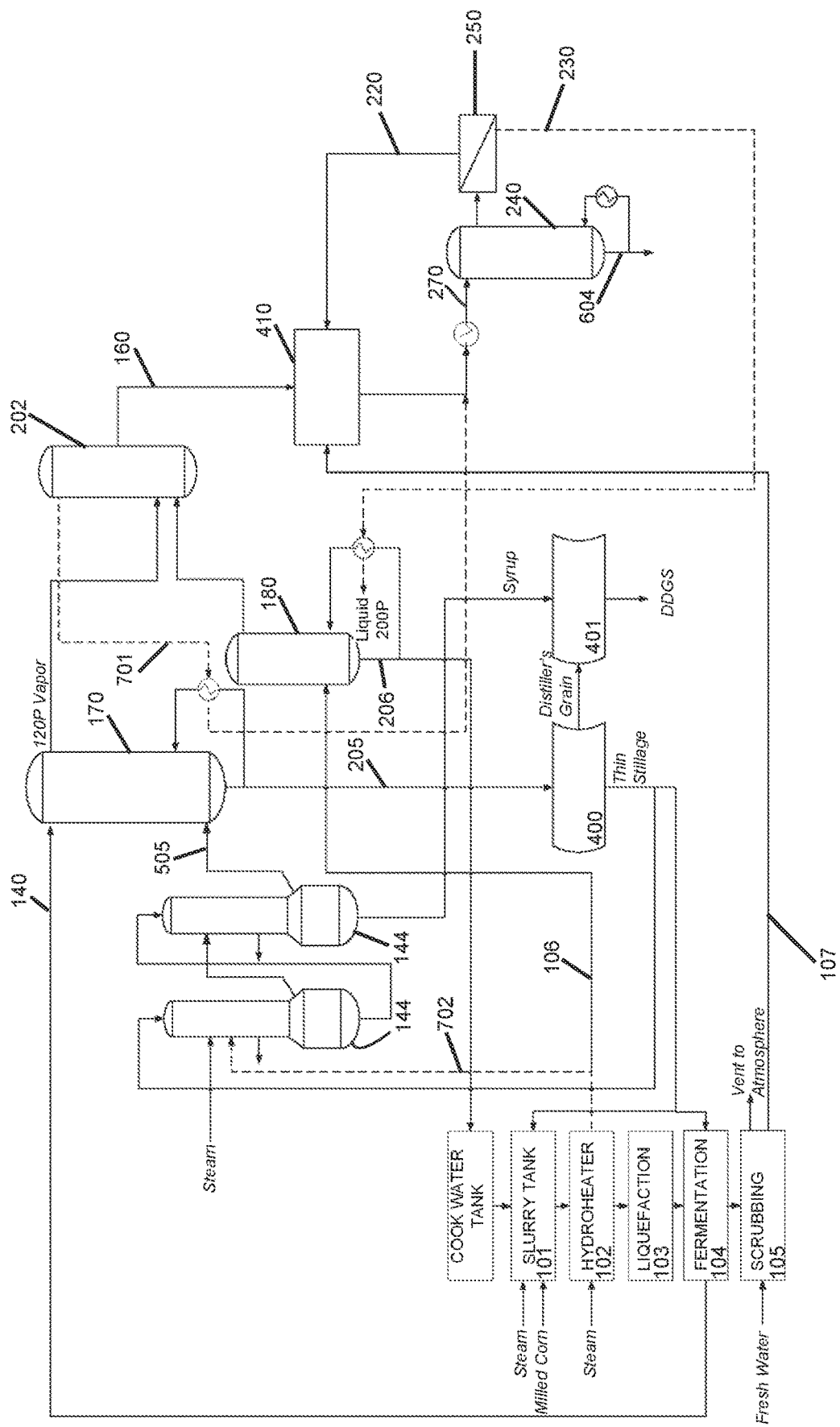
FIG. 8 is a schematic illustration of yet another non-limiting example embodiment of a system for heat integration in ethanol production according to the present disclosure.

Referring to FIG. 8, in the illustrated embodiment the rectifier column 202 operates as a stripper column, thereby eliminating the need of a 190-proof ethanol vapor condenser and reducing the cooling water consumption. At least one beer column reboiler is operated with the overhead stream 701 from the rectifier column 202. The condensed overhead stream is processed in the separation system 240, 250. The energy in the retentate 230 is used to operate the side stripper reboiler. The evaporators are operated at least in part with the steam 702 from the hydroheater, as the side stripper no longer needs the steam 702 from the hydroheater.

FIGS. 9-30 illustrate processes and systems for recovering heat energy according to another embodiment of the invention, by adding more heat exchangers and/or modifying the heat recovery configurations. A benefit of the processes and systems for heat integration in ethanol production according to these embodiments is that the energy of the MSU product vapor can be better or fully recuperated before the MSU product is injected as a liquid at the top of the ARC.

Figure 9:
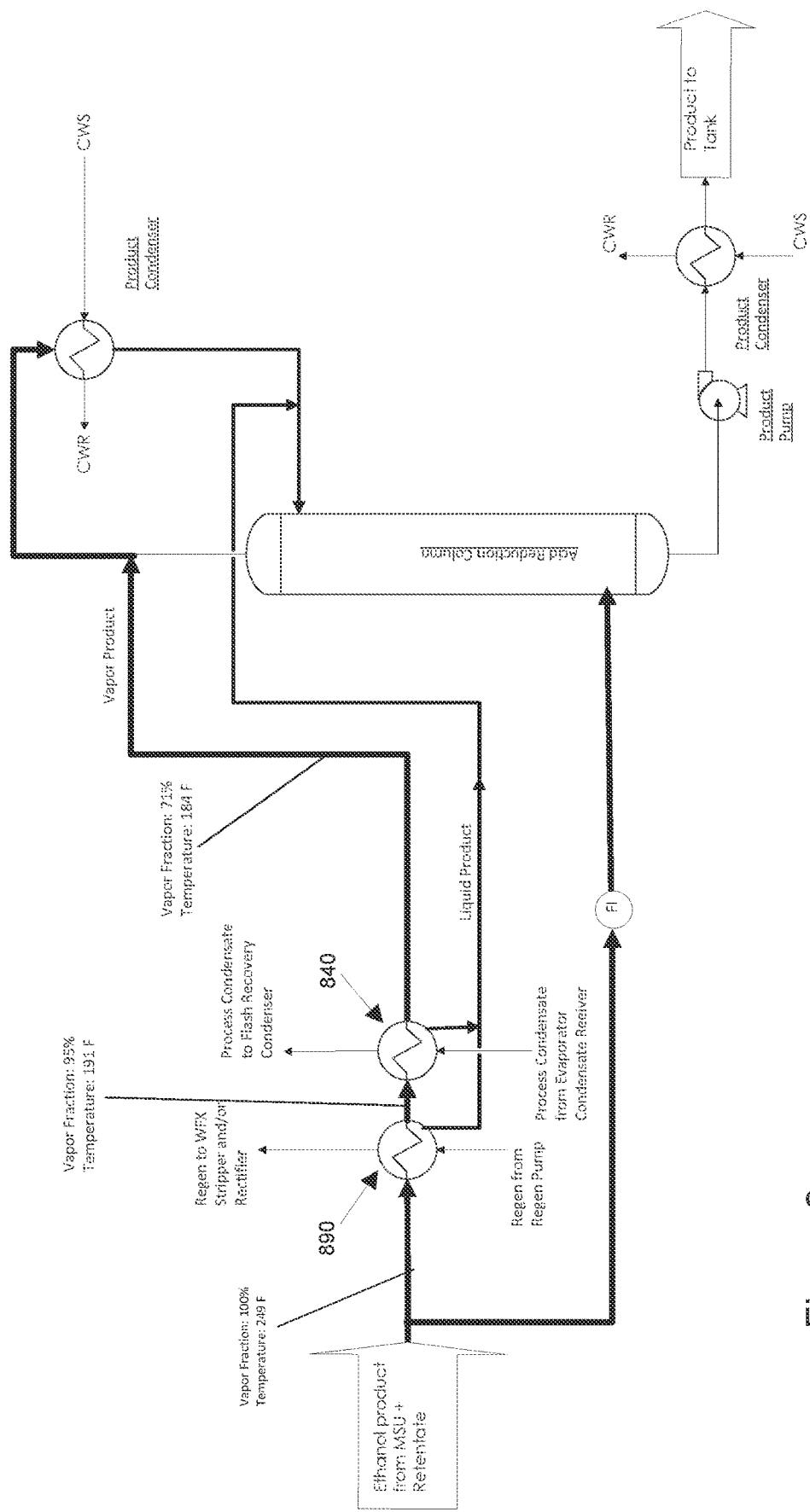
FIG. 9 is a schematic illustration of yet another non-limiting example embodiment of a system for heat integration in ethanol production according to the present disclosure.
Figure 10:
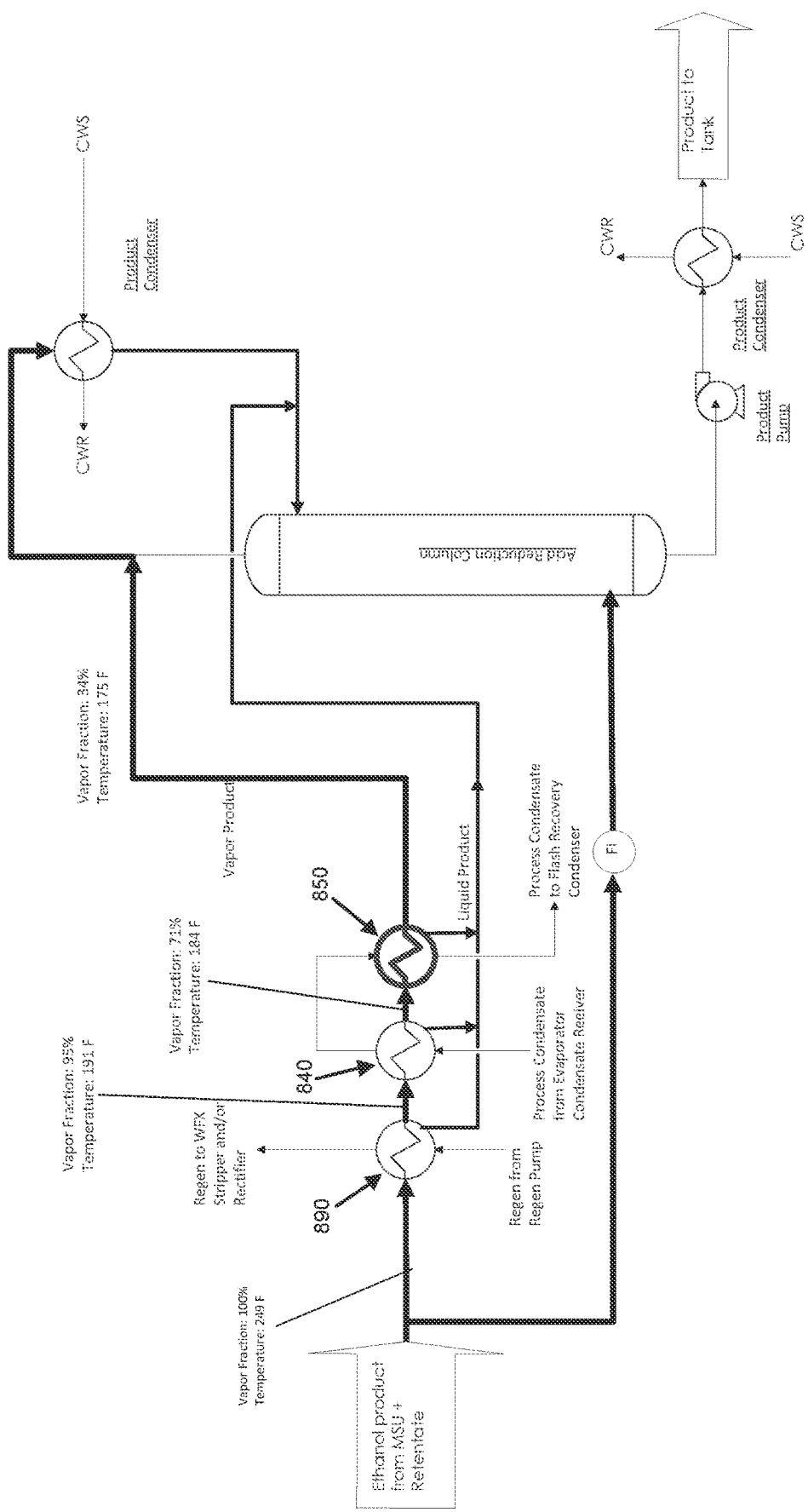
FIG. 10 is a schematic illustration of yet another non-limiting example embodiment of a system for heat integration in ethanol production according to the present disclosure.

Referring to FIG. 9, in the illustrated embodiment a retentate is added to the ethanol product. Referring to FIG. 10, in the illustrated embodiment a heat exchanger 850 is added to the embodiment illustrated in FIG. 9. In the embodiment illustrated in FIG. 10, the process condensate firstly passes through the current condensate preheater 840, then through the new condensate preheater 850. The energy recuperated in the embodiment illustrated in FIG. 10 is about 760 BTU/gal.

Figure 11:
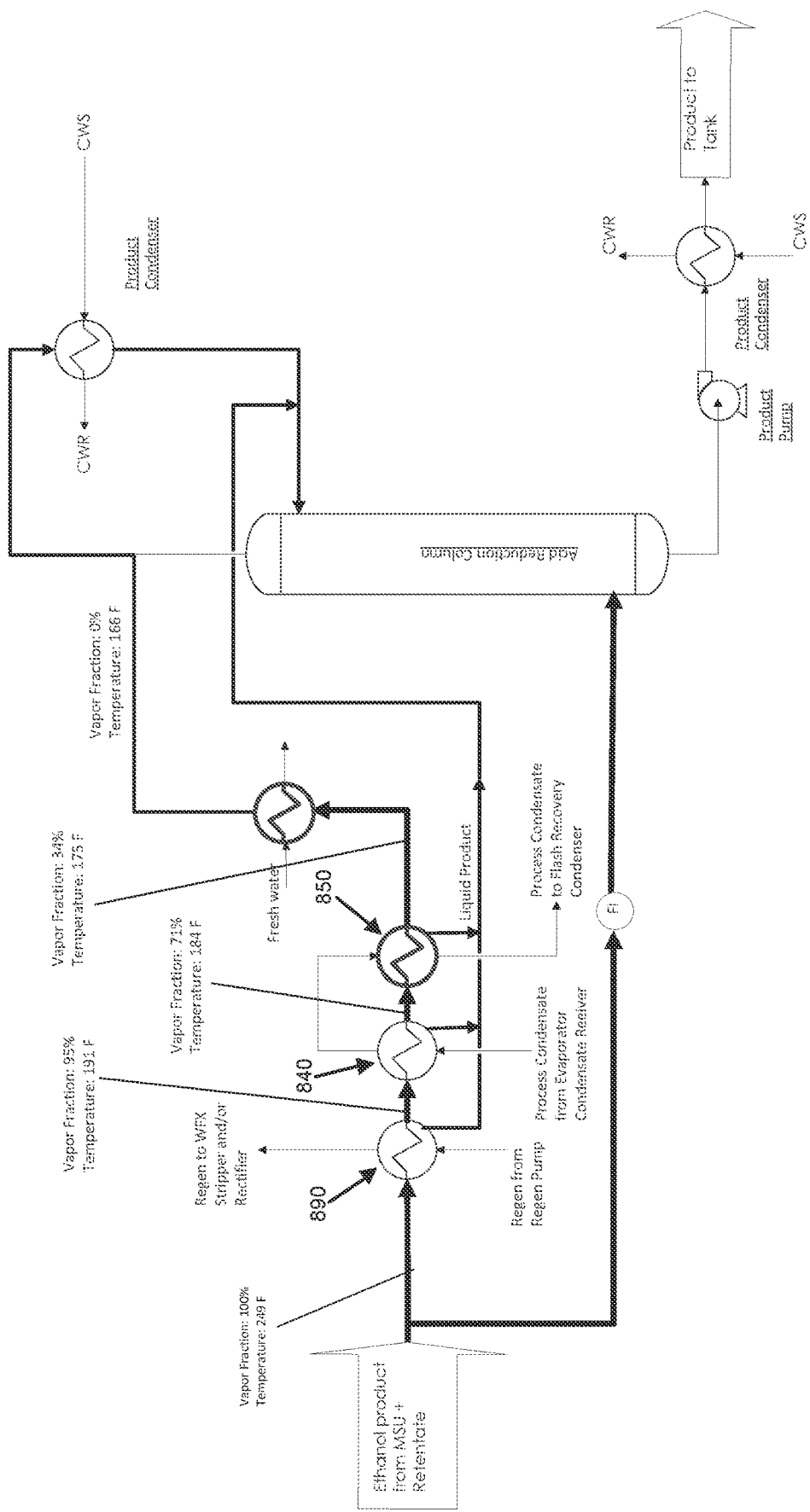
FIG. 11 is a schematic illustration of yet another non-limiting example embodiment of a system for heat integration in ethanol production according to the present disclosure.

Referring to FIG. 11, an embodiment is shown with complete condensation of the MSU product vapor by heating a low-temperature flow (in the example this flow is fresh water; however, any other low temperature flow can be used). The heat recuperated is equivalent to about 1,470 BTU/gal.

Referring to FIGS. 12-30, in the illustrated embodiments the heat from MSU ethanol product (200P) and retentate (ethanol product) heat are recovered. In some prior systems for producing ethanol from feedstock, the remaining vapor product is about 34% of the total ethanol product, and is condensed and cooled down by cooling water, as presented in Table 1.

TABLE 1

|  | Ethanol Product from MSU + Retentate from WFX ICE | |
| --- | --- | --- |
|  | Vapor Frac. | Temperature, F. |
| Ethanol product before Regen Condenser | 1 | 249 |
| Ethanol product after Regen Condenser | 0.95 | 191 |
| Ethanol product after Condensate Preheater | 0.71 | 184 |
| Ethanol product after a new Condensate Preheater | 0.34 | 175 |

Figure 12:
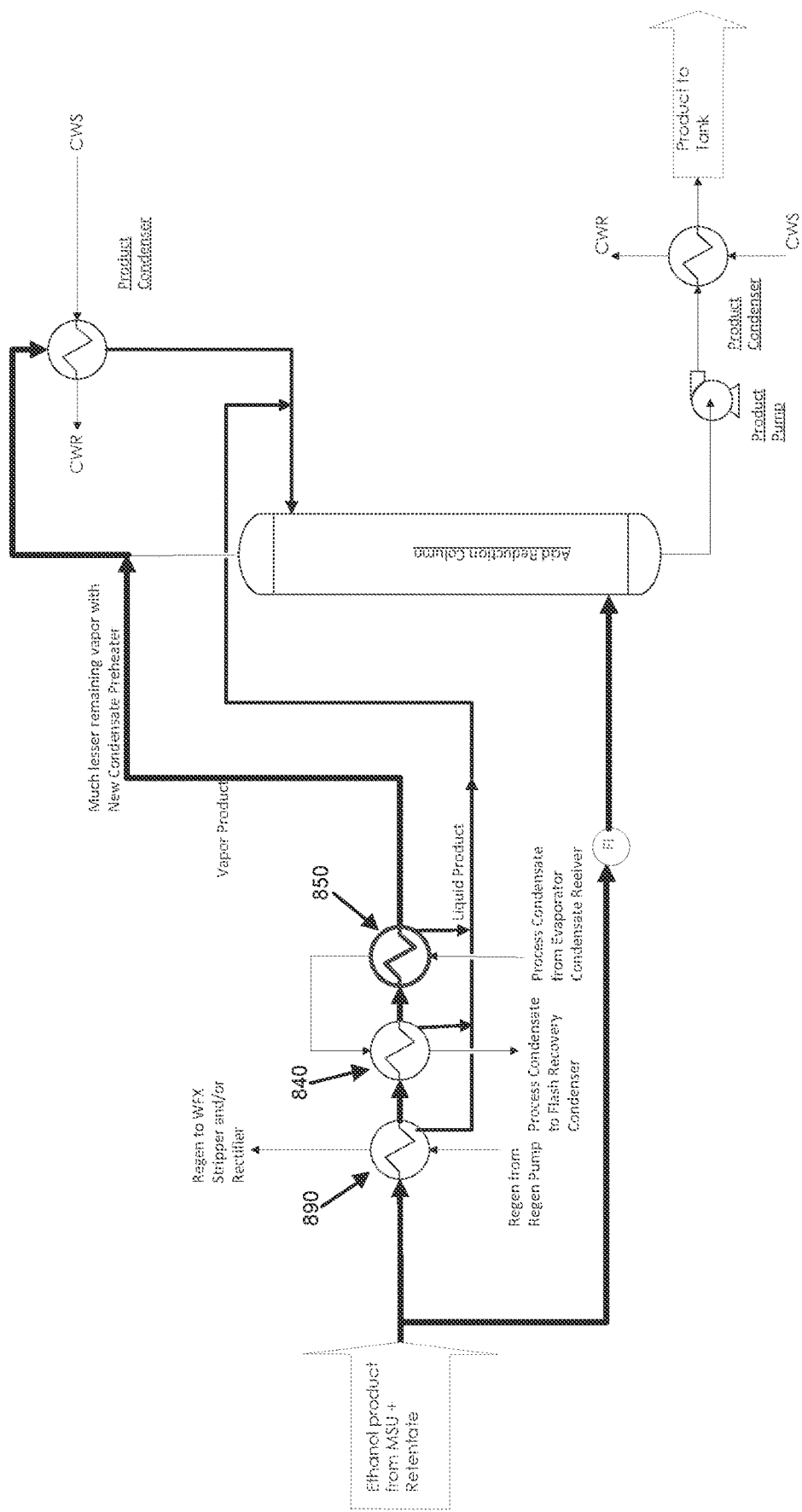
FIG. 12 is a schematic illustration of yet another non-limiting example embodiment of a system for heat integration in ethanol production according to the present disclosure.

Referring to FIG. 12, the illustrated embodiment increases energy recovery by sending the process condensate through the new condensate preheater 850, then through the current condensate preheater 840.

Figure 13:
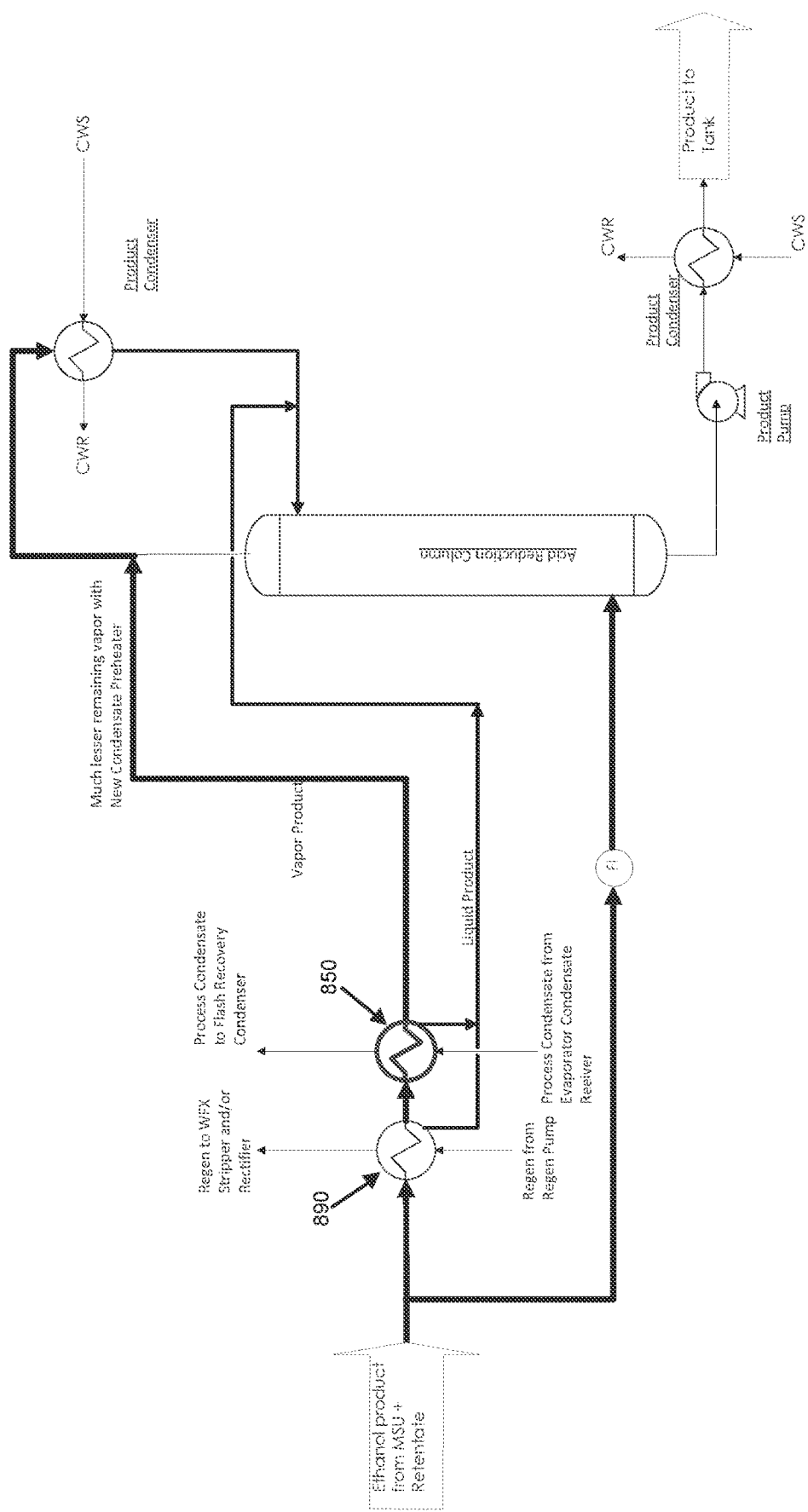
FIG. 13 is a schematic illustration of yet another non-limiting example embodiment of a system for heat integration in ethanol production according to the present disclosure.

Referring to FIG. 13, the illustrated embodiment replaces the current condensate preheater with a condensate preheater 850 of larger capacity to recover as much heat energy as possible from the product ethanol. This embodiment employs much of the same structure as the embodiment described above in connection with FIG. 12, except that this embodiment has less heat exchangers.

Figure 14:
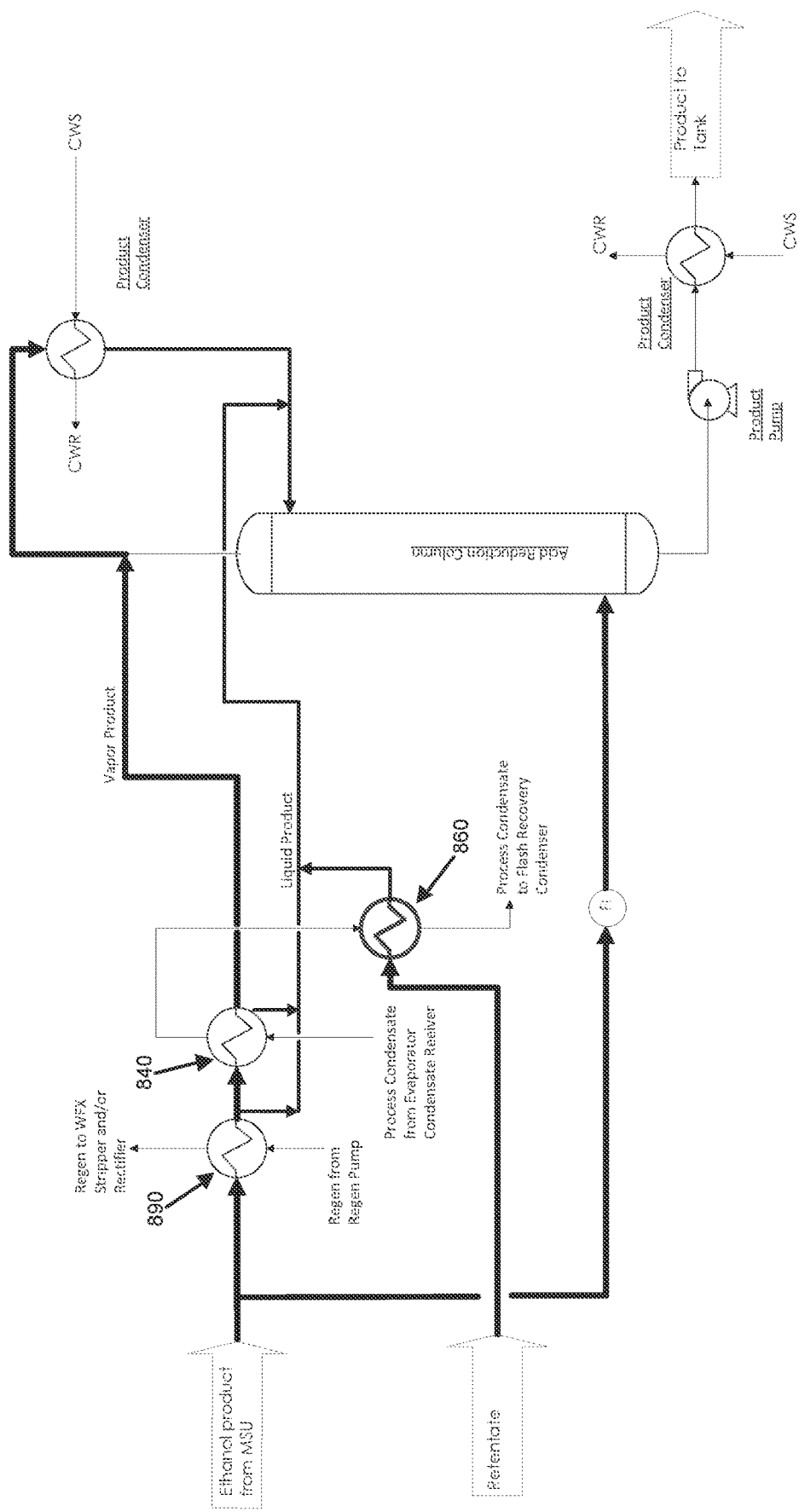
FIG. 14 is a schematic illustration of yet another non-limiting example embodiment of a system for heat integration in ethanol production according to the present disclosure.

Referring to FIG. 14, in the illustrated embodiment the process condensate firstly passes through the current condensate preheater 840, then through a new retentate condenser 860 to recover the heat energy from the retentate. In certain non-limiting embodiments, the remaining energy from MSU ethanol product may not be further recovered.

Figure 15:
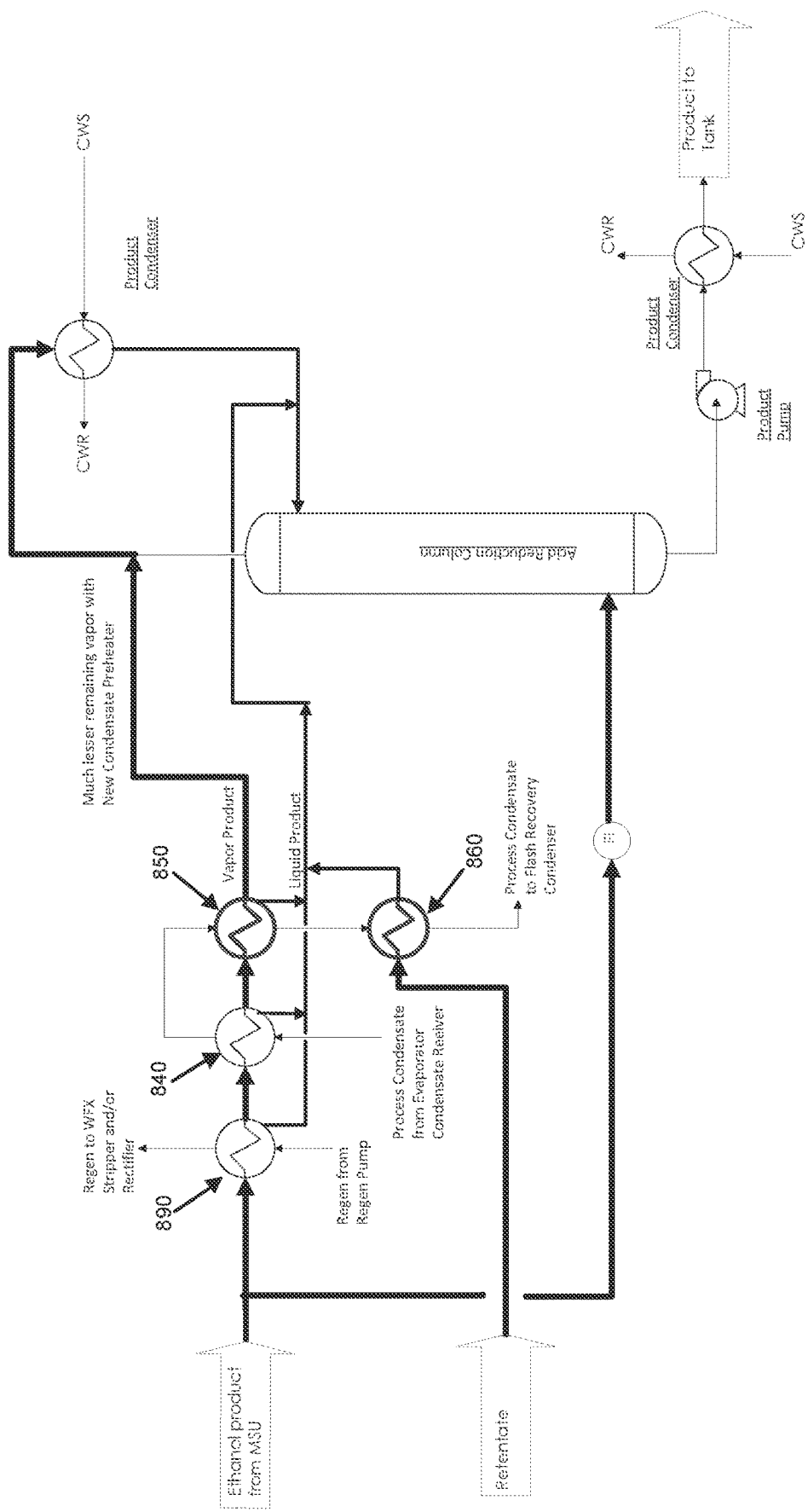
FIG. 15 is a schematic illustration of yet another non-limiting example embodiment of a system for heat integration in ethanol production according to the present disclosure.

Referring to FIG. 15, in the illustrated embodiment the process condensate firstly passes through the current condensate preheater 840, then through a new condensate preheater 850 to further recover the heat energy from MSU ethanol product. Then the process condensate passes through a new retentate condenser 860 to recover the heat energy from retentate.

Figure 16:
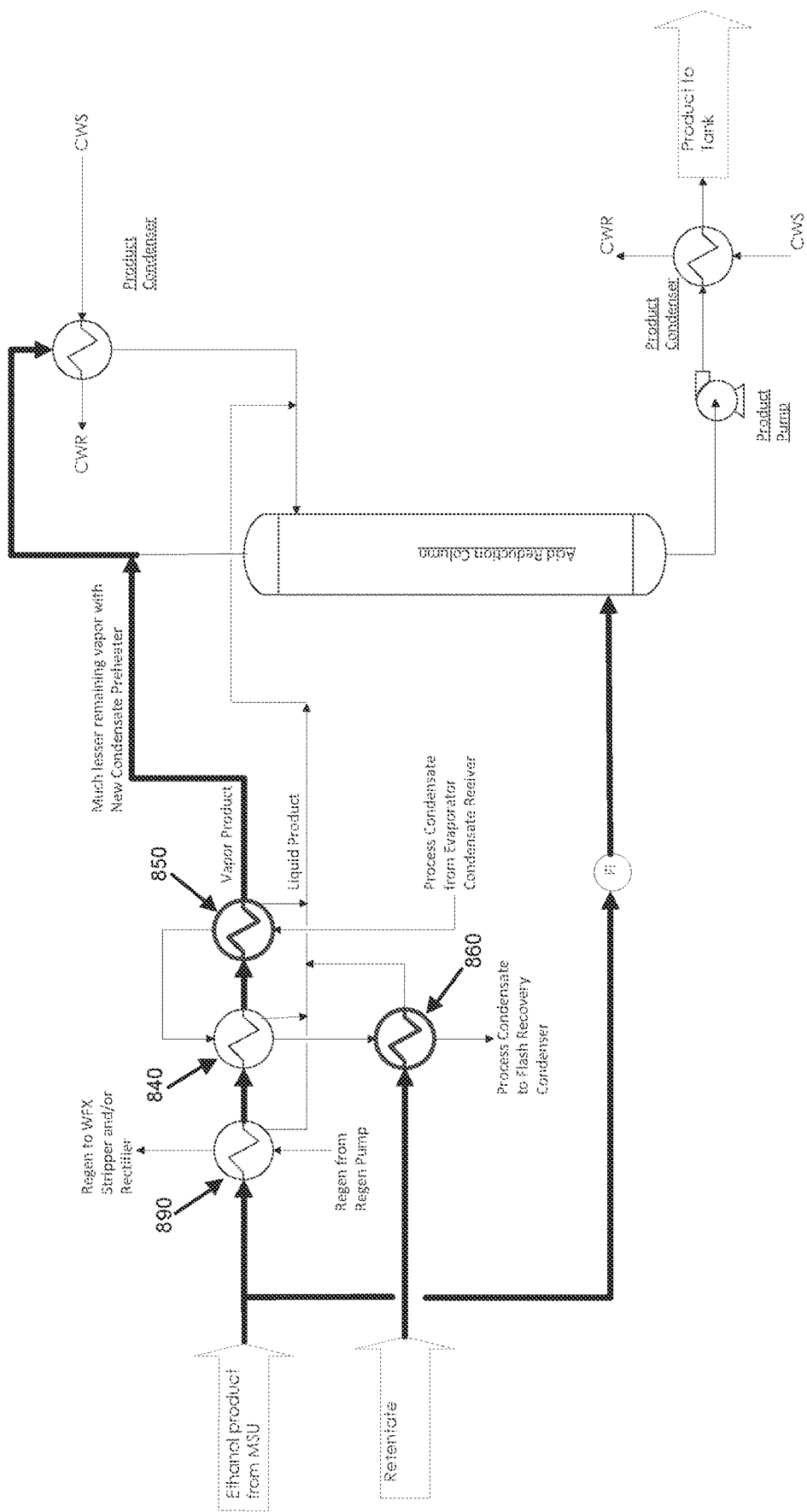
FIG. 16 is a schematic illustration of yet another non-limiting example embodiment of a system for heat integration in ethanol production according to the present disclosure.

Referring to FIG. 16, in the illustrated embodiment the process condensate firstly passes through a new condensate preheater 850, then through the current condensate preheater 840 to recover the heat energy from MSU ethanol product. Then the process condensate passes through a new retentate condenser 860 to recover the heat energy from retentate. Although this configuration may require more changes on the piping, it can achieve more efficient energy recovery.

Figure 17:
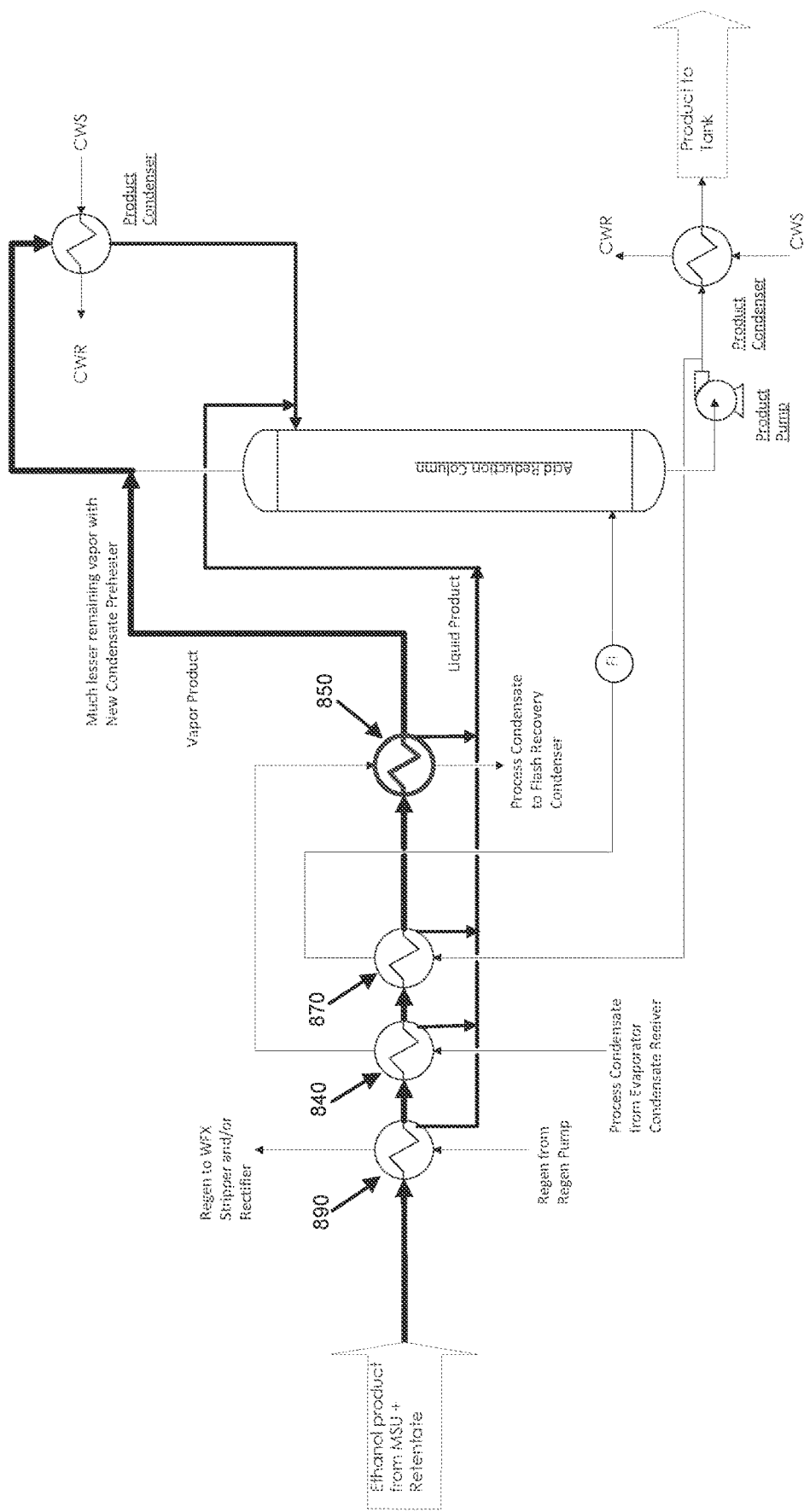
FIG. 17 is a schematic illustration of yet another non-limiting example embodiment of a system for heat integration in ethanol production according to the present disclosure.

Referring to FIG. 17, in the illustrated embodiment the process condensate firstly passes through the current condensate preheater 840, then through a new condensate preheater 850 which is located after the acid reduction reboiler 870.

Figure 18:
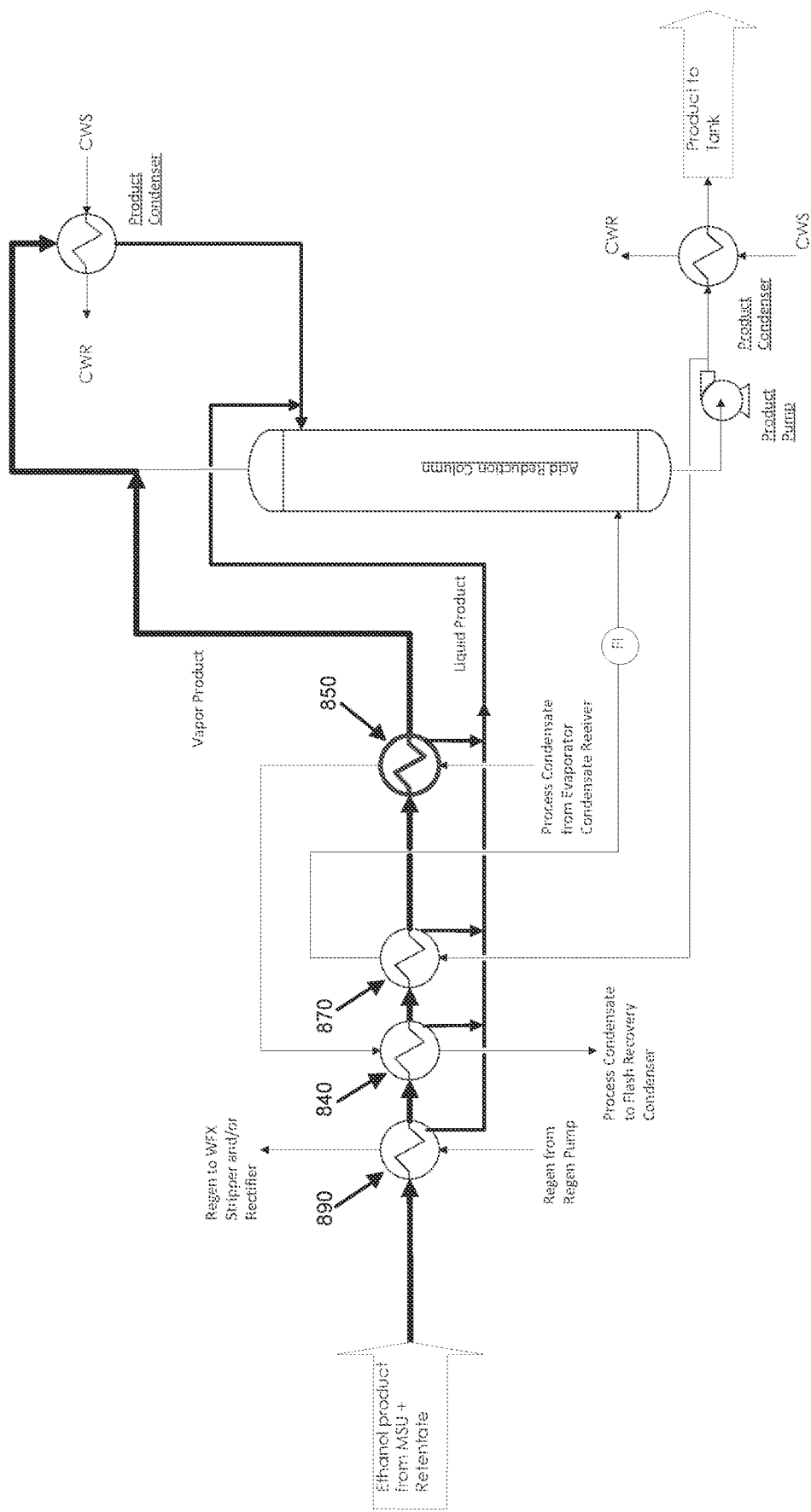
FIG. 18 is a schematic illustration of yet another non-limiting example embodiment of a system for heat integration in ethanol production according to the present disclosure.

Referring to FIG. 18, the illustrated embodiment increases the energy recovery by sending the process condensate through a new condensate preheater 850 which is located after the acid reduction reboiler 870, then through the current condensate preheater 840.

Figure 19:
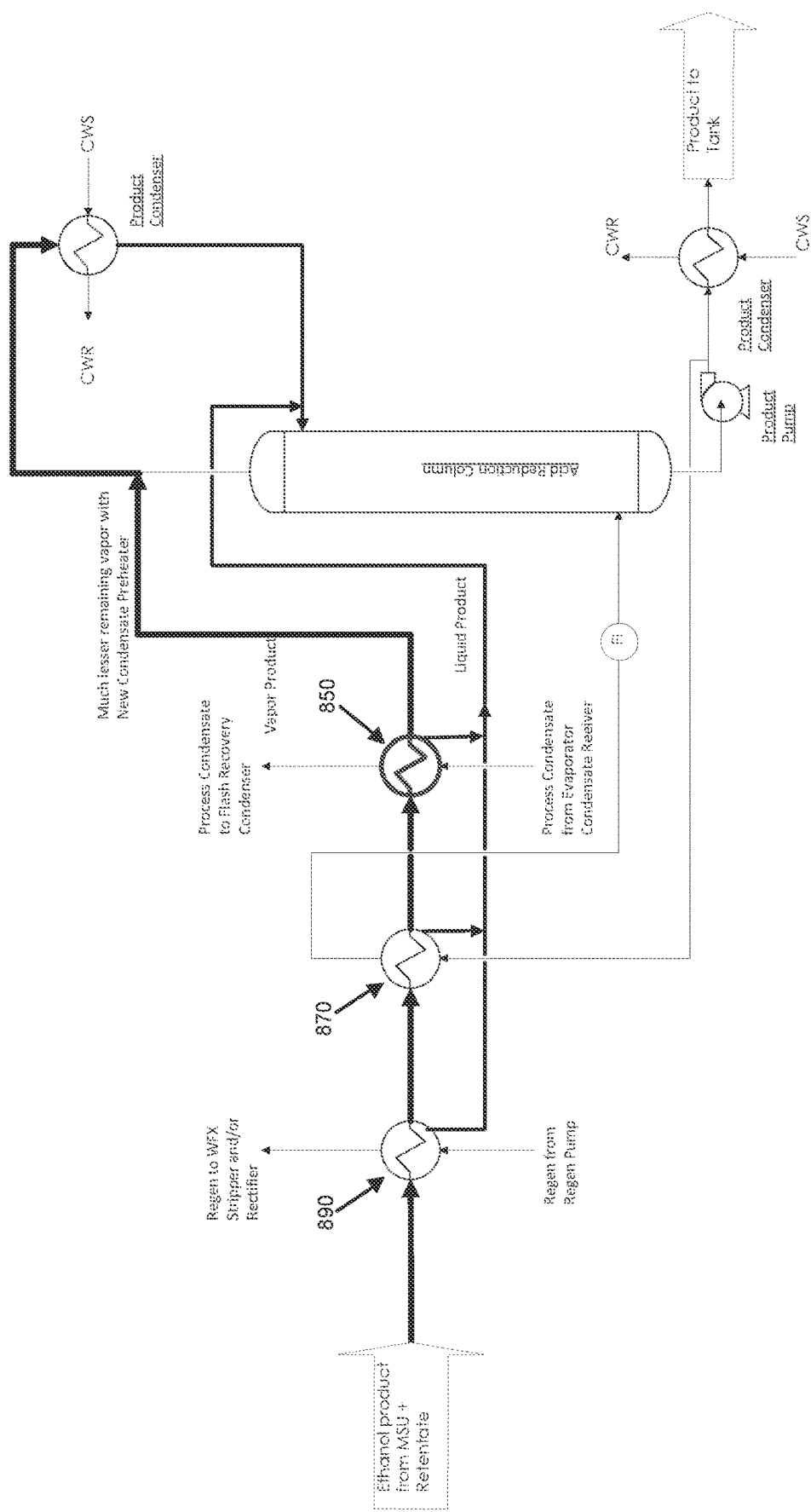
FIG. 19 is a schematic illustration of yet another non-limiting example embodiment of a system for heat integration in ethanol production according to the present disclosure.

Referring to FIG. 19, in the illustrated embodiment the current condensate preheater is removed, and a larger capacity of condensate preheater 850 is added after the acid reduction reboiler 870 to recover as much heat energy as possible from the product ethanol. This embodiment employs much of the same structure as the embodiment described above in connection with FIG. 18, except that this embodiment has less heat exchangers.

Figure 20:
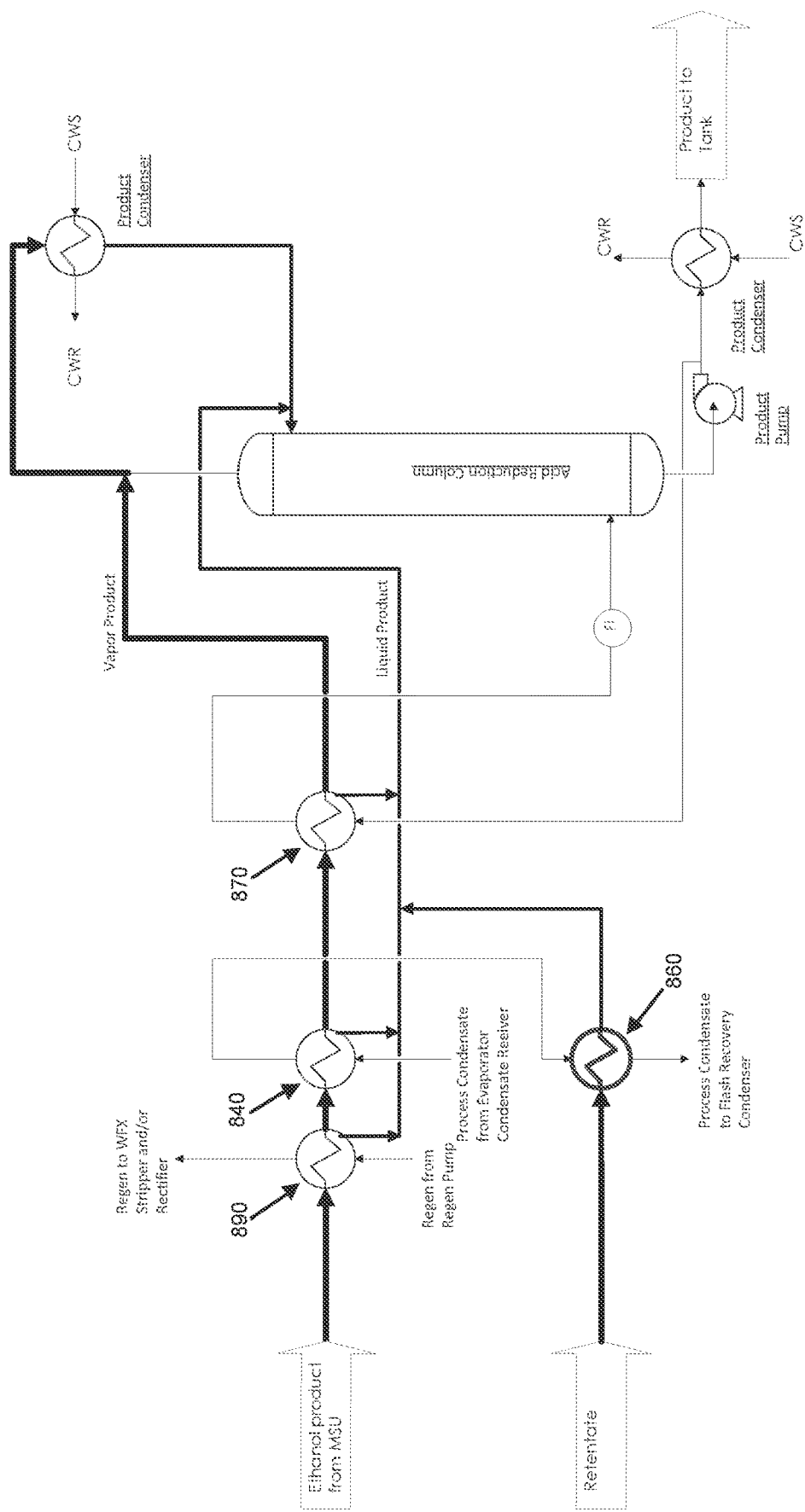
FIG. 20 is a schematic illustration of yet another non-limiting example embodiment of a system for heat integration in ethanol production according to the present disclosure.

Referring to FIG. 20, in the illustrated embodiment the process condensate firstly passes through current condensate preheater 840, then through a new retentate condenser 860 to recover the heat energy from the retentate. In certain non-limiting embodiments, the remaining energy from MSU ethanol product may not be further recovered.

Figure 21:
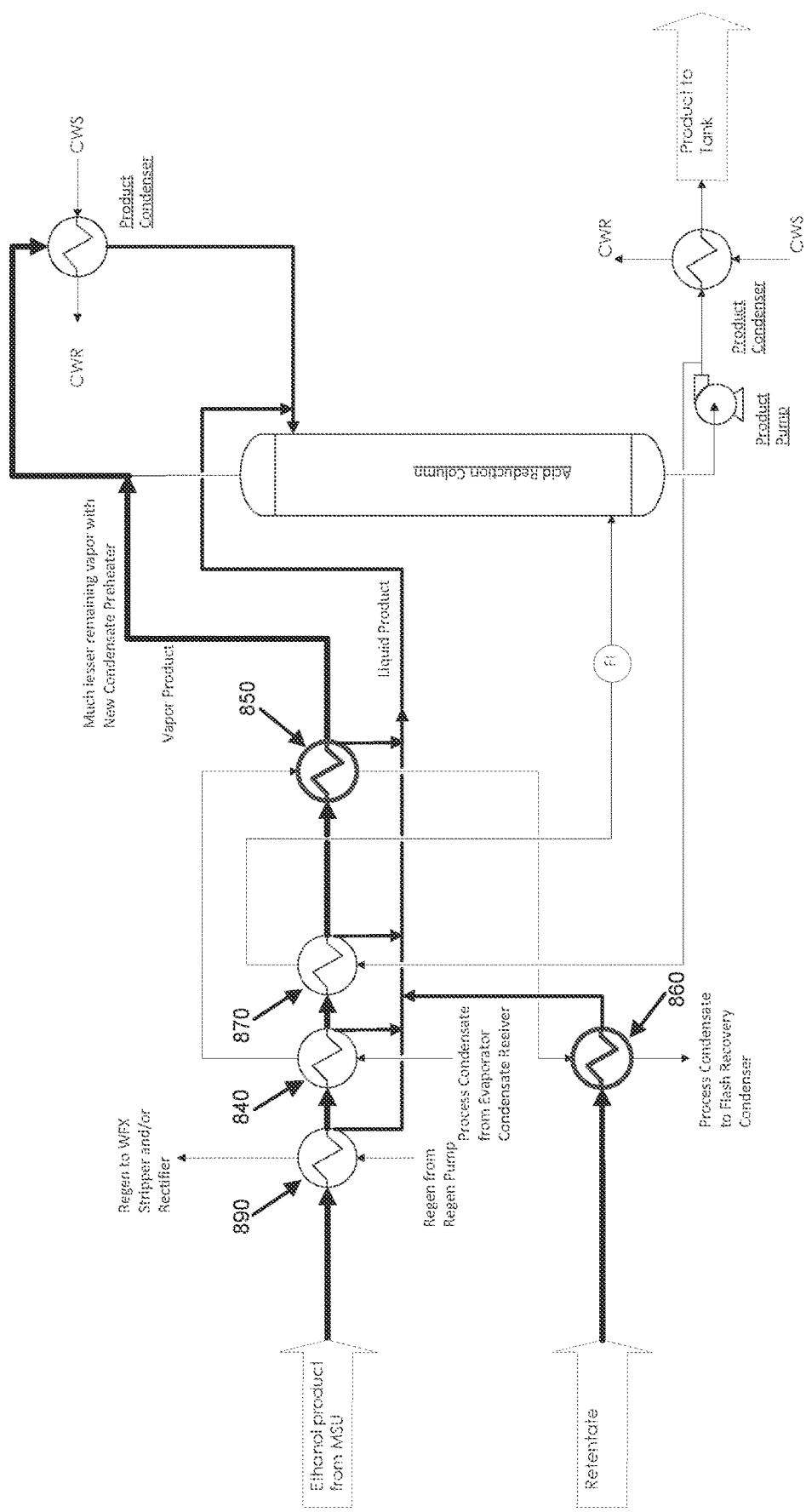
FIG. 21 is a schematic illustration of yet another non-limiting example embodiment of a system for heat integration in ethanol production according to the present disclosure.

Referring to FIG. 21, in the illustrated embodiment the process condensate firstly passes through current condensate preheater 840, then through a new condensate preheater 850 (after the acid reduction boiler 870) to further recover the heat energy from MSU ethanol product. Then the process condensate passes through a new retentate condenser 860 to recover the heat energy from the retentate.

Figure 22:
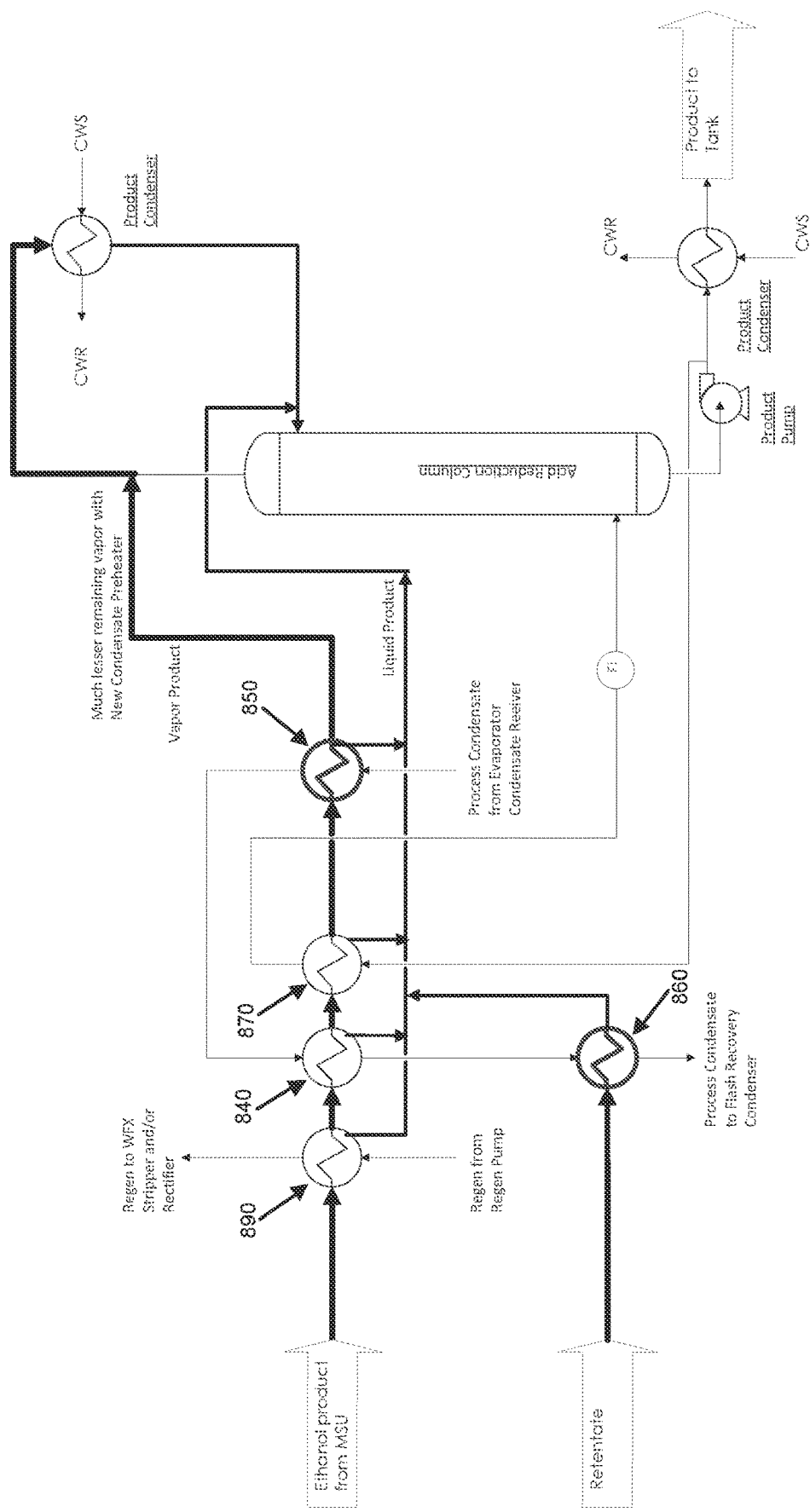
FIG. 22 is a schematic illustration of yet another non-limiting example embodiment of a system for heat integration in ethanol production according to the present disclosure.

Referring to FIG. 22, in the illustrated embodiment process the condensate firstly passes through a new condensate preheater 850 (after the acid reduction boiler 870), then through the current condensate preheater 840 to recover the heat energy from the MSU ethanol product. Then the process condensate passes through a new retentate condenser 860 to recover the heat energy from retentate. Although this configuration may require more changes on piping, it can achieve more efficient energy recovery.

Figure 23:
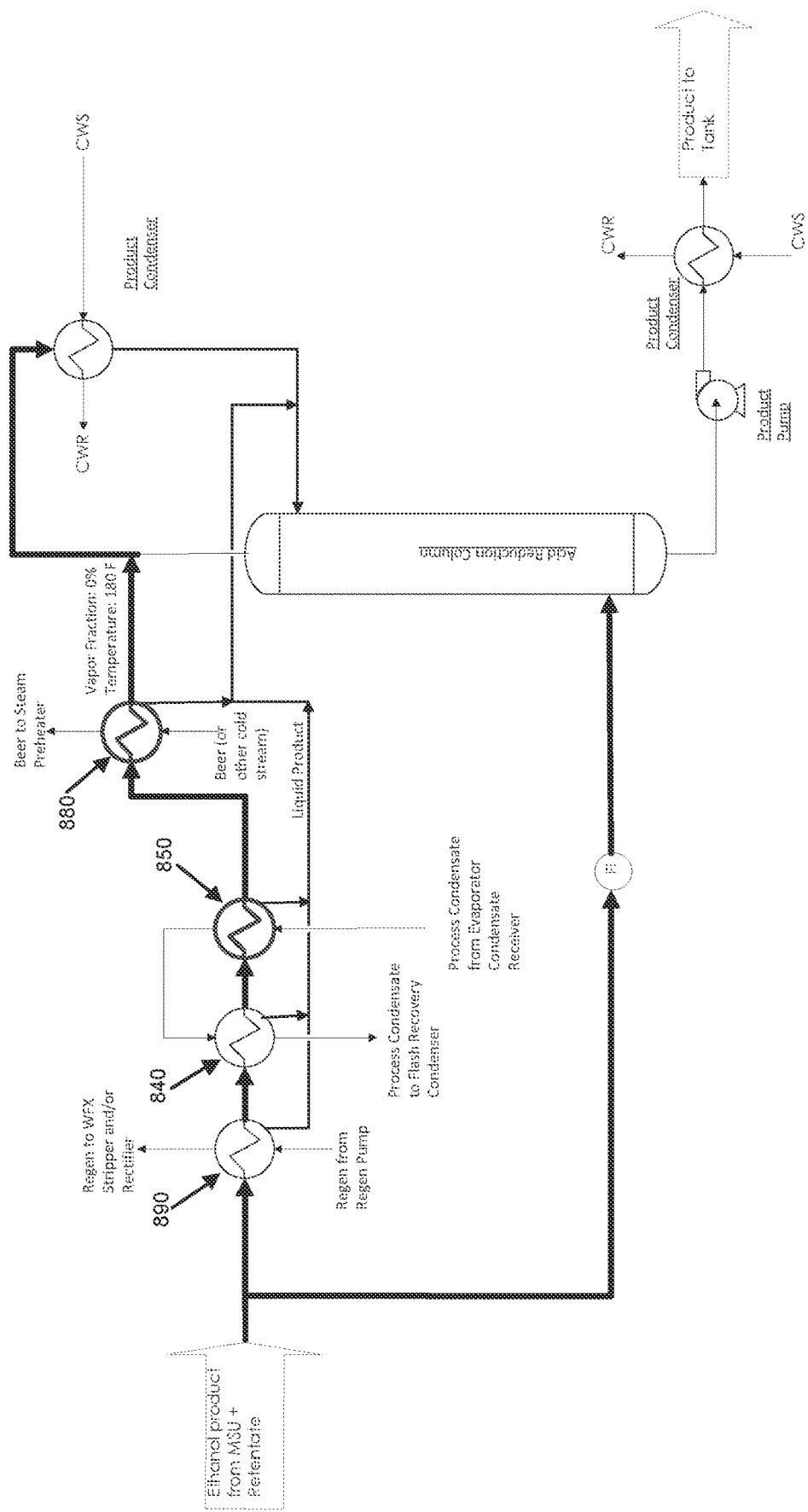
FIG. 23 is a schematic illustration of yet another non-limiting example embodiment of a system for heat integration in ethanol production according to the present disclosure.

Referring to FIG. 23, the illustrated embodiment employs much of the same structure as the embodiment described above in connection with FIG. 18, and additionally includes a new beer preheater 880. The mixture of MSU product vapor and retentate passes through the current regen preheater 890 and condensate preheater 840, and then passes through a new condensate preheater 850 and the new beer preheater 880. By heating the beer feed, and the MSU product vapor and retentate vapor are condensed. The energy recuperated in the embodiment illustrated in FIG. 23 is equivalent to 1,460 BTU/gal.

Figure 24:
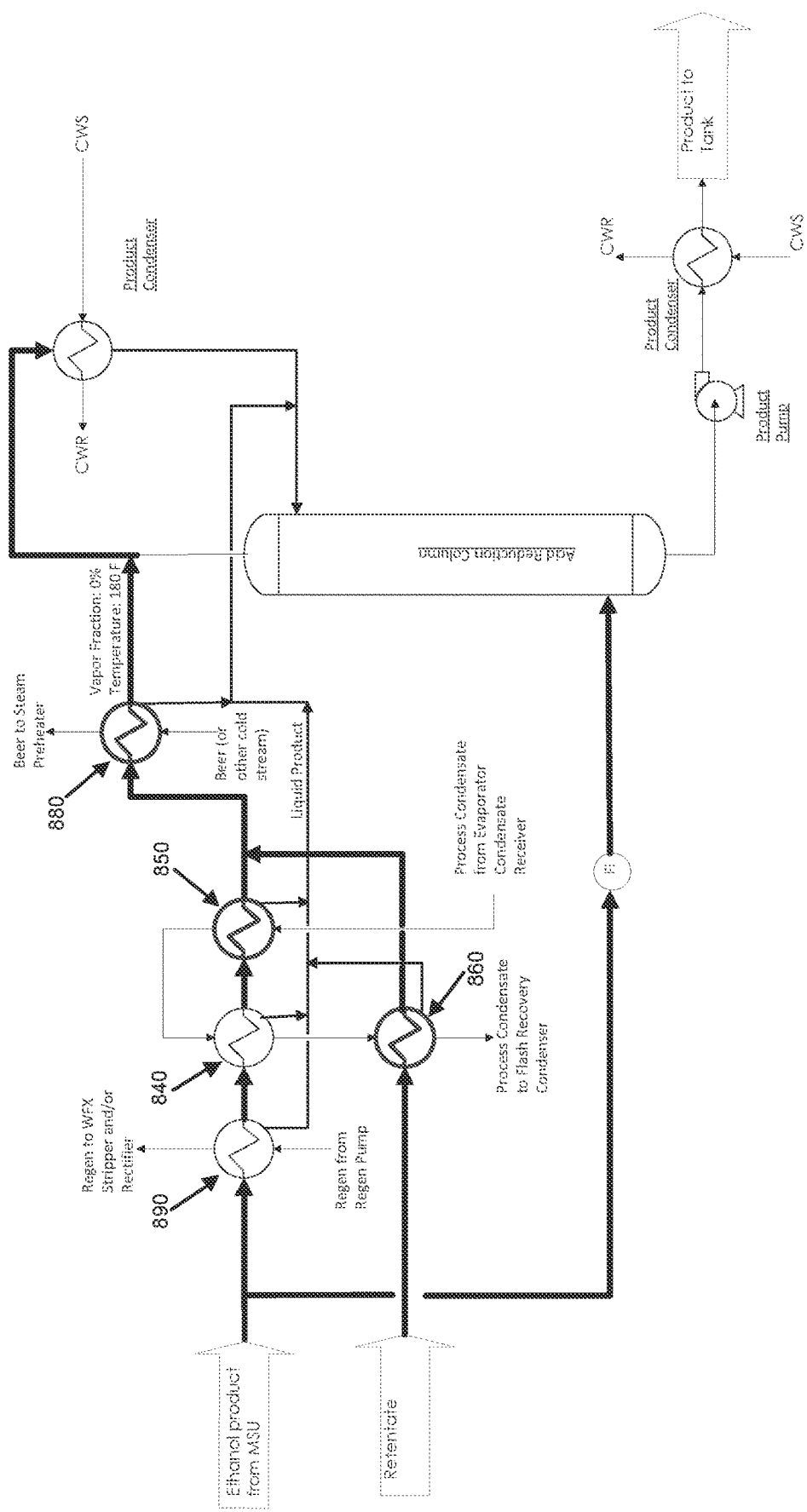
FIG. 24 is a schematic illustration of yet another non-limiting example embodiment of a system for heat integration in ethanol production according to the present disclosure.

Referring to FIG. 24, the illustrated embodiment employs much of the same structure as the embodiment described above in connection with FIG. 16, and additionally includes a new beer preheater 880. Uncondensed vapor from MSU product and retentate passes through the new beer preheater 880 and is condensed by heating up the beer feed before beer is heated by steam. The energy recuperated in the embodiment illustrated in FIG. 24 is equivalent to 1,500 BTU/gal.

Figure 25:
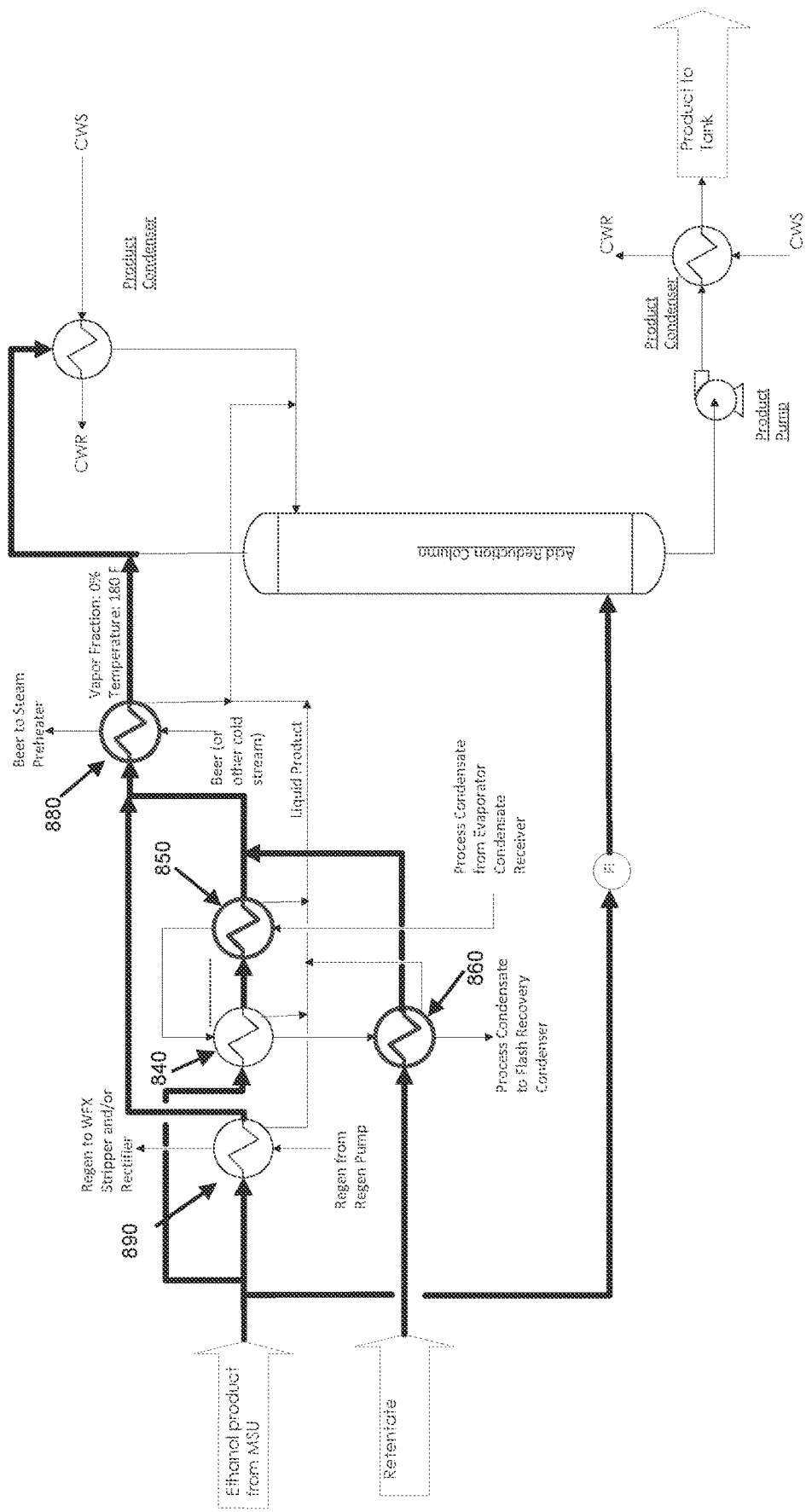
FIG. 25 is a schematic illustration of yet another non-limiting example embodiment of a system for heat integration in ethanol production according to the present disclosure.

Referring to FIG. 25, the illustrated embodiment employs much of the same structure as the embodiment described above in connection with FIG. 24, except that in this embodiment the ethanol product from MSU is separately entering the regen preheater 890 and the condensate preheater. The energy recuperated in the embodiment illustrated in FIG. 25 is equivalent to 1,500 BTU/gal.

Figure 26:
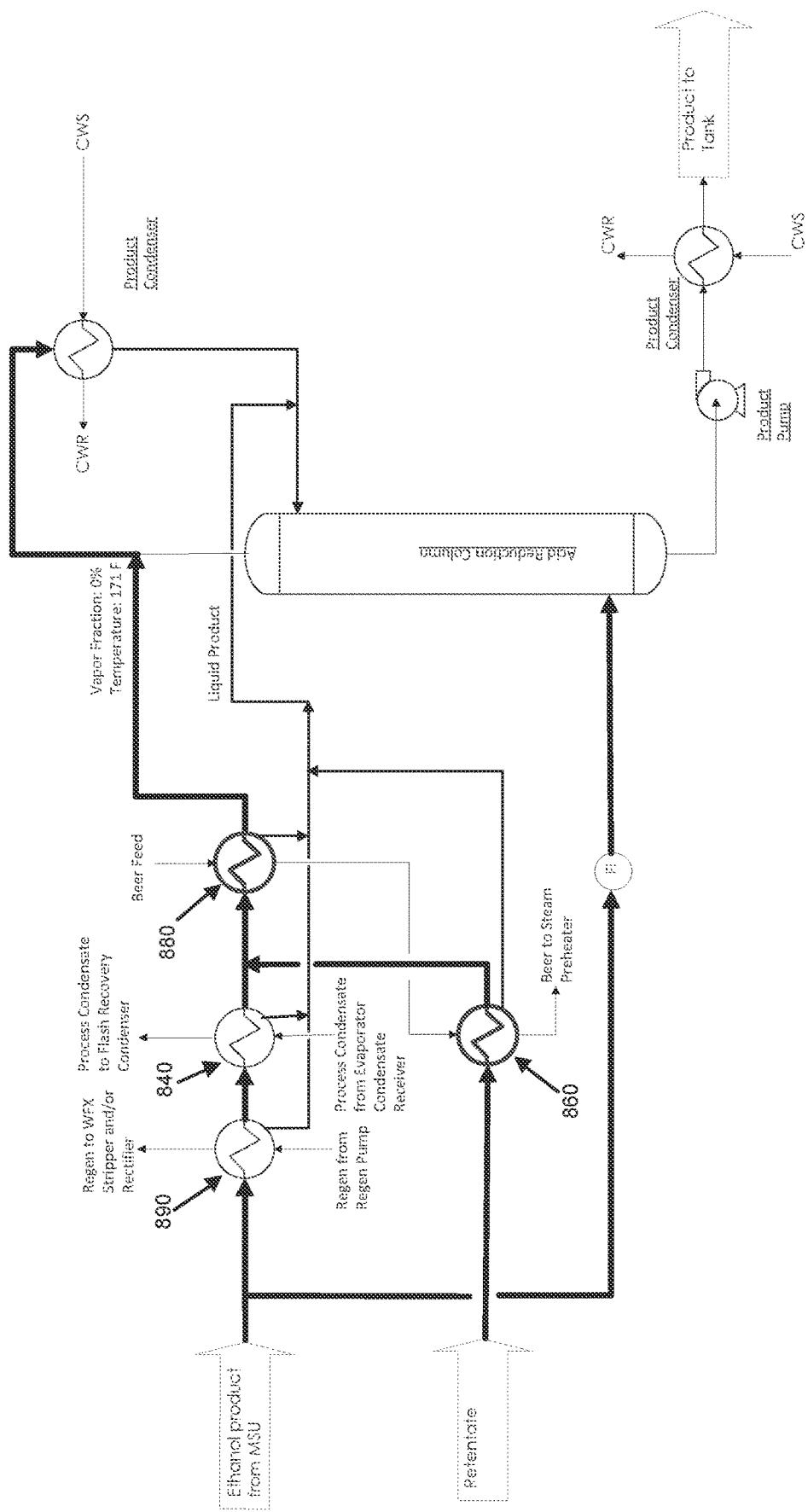
FIG. 26 is a schematic illustration of yet another non-limiting example embodiment of a system for heat integration in ethanol production according to the present disclosure.

Referring to FIG. 26, the illustrated embodiment employs much of the same structure as the embodiment described above in connection with FIG. 16, except that in this embodiment the new condensate preheater is replaced with a new beer preheater 880. In this embodiment, MSU product vapor passes through the current regen preheater 890 and the condensate preheater 840, then passes through the new beer preheater 880, and the vapor is condensed. The heated beer from the new beer preheater 880 passes through the retentate condenser 860 and is further heated up while the retentate vapor is condensed. Remaining vapor from the retentate condenser 860 is mixed with the MSU product vapor before entering the new beer preheater 880. The energy recuperated in the illustrated embodiment is equivalent to 1,380 BTU/gal.

Figure 27:
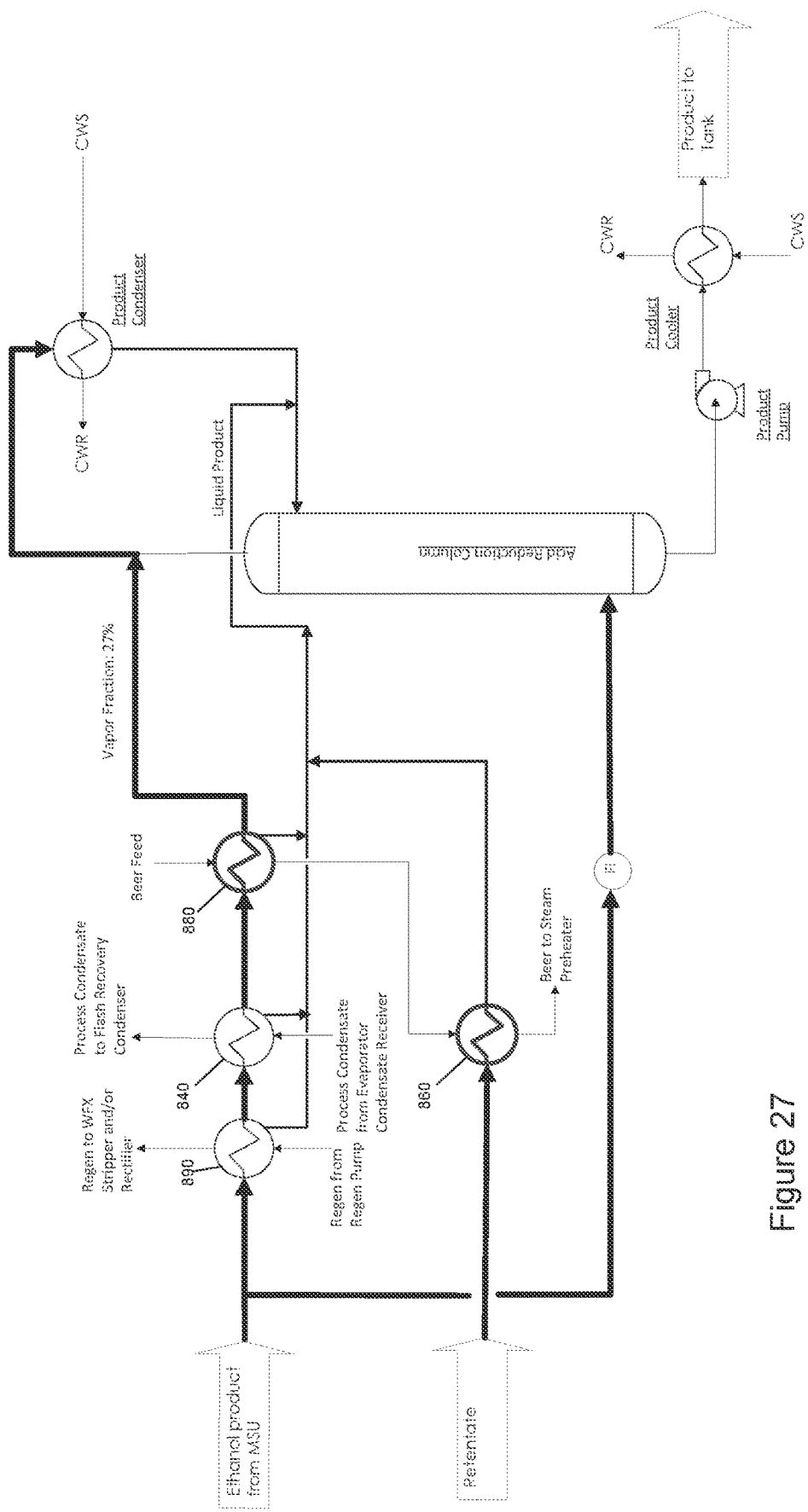
FIG. 27 is a schematic illustration of yet another non-limiting example embodiment of a system for heat integration in ethanol production according to the present disclosure.

Referring to FIG. 27, in the illustrated embodiment MSU product vapor passes through the current regen preheater 890 and condensate preheater 840, then passes through a new beer preheater 880 to get most of the vapors condensed. The heated beer from the new beer preheater 880 passes through a retentate condenser 860 to get further heated up while substantially all of the retentate vapors are condensed. The condensed retentate is sent to the liquid line to the acid reduction column. The heat recuperated in the illustrated embodiment is equivalent to up to 1,240 BTU/gal.

Figure 28:
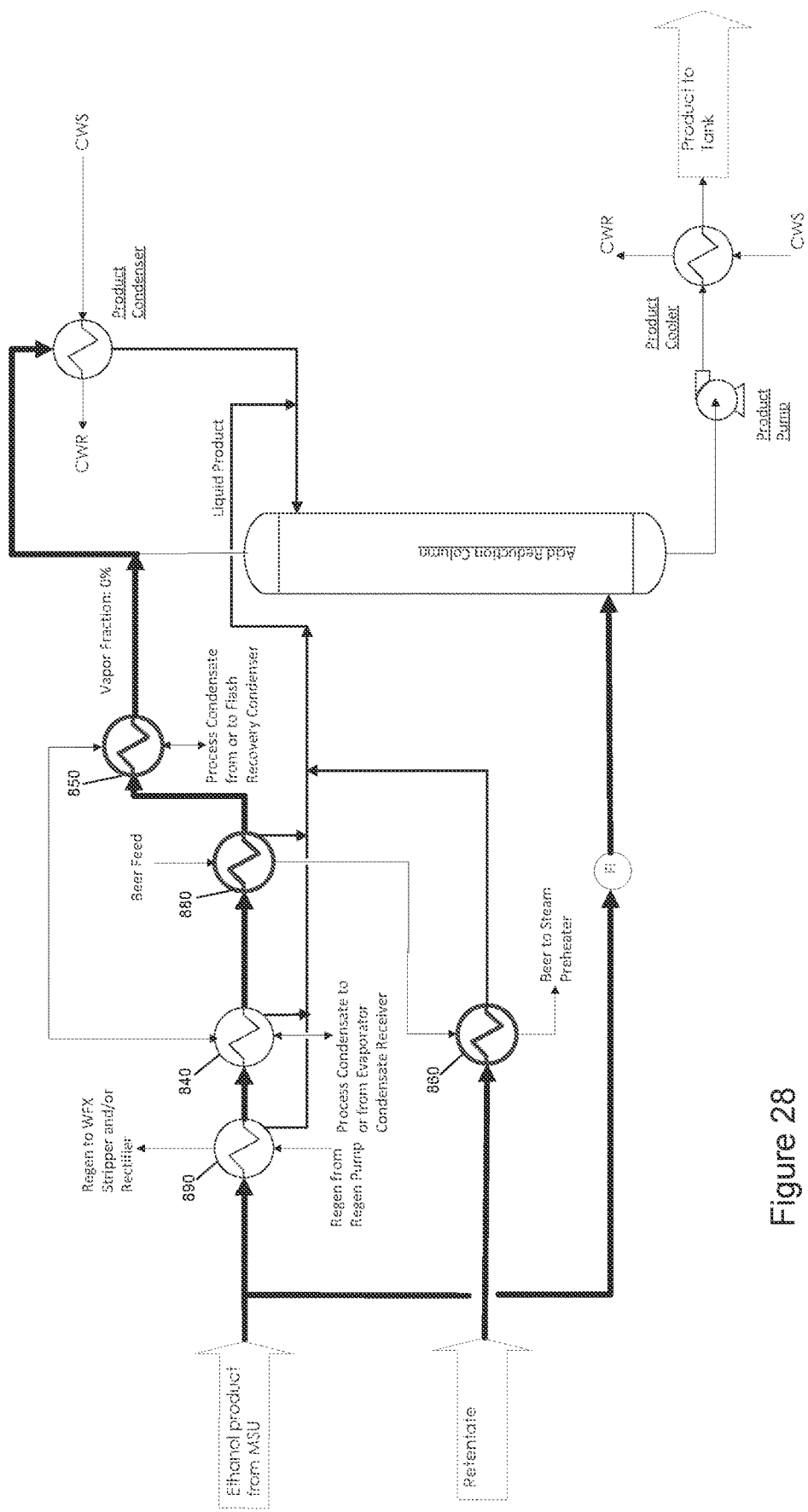
FIG. 28 is a schematic illustration of yet another non-limiting example embodiment of a system for heat integration in ethanol production according to the present disclosure.

Referring to FIG. 28, the illustrated embodiment employs much of the same structure as the embodiment described above in connection with FIG. 27, and additionally includes a new condensate preheater 850 to get the MSU product vapor completely condensed. The process condensate can be sent to the existing condensate preheater 840 then to the new condensate preheater 850 to minimize the installation cost, or it can be sent to the new condensate preheater 850 and then to the existing condensate preheater 840 to maximize the heat recovery efficiency. The heat recuperated in the illustrated embodiment is equivalent to up to 1,600 BTU/gal.

Figure 29:
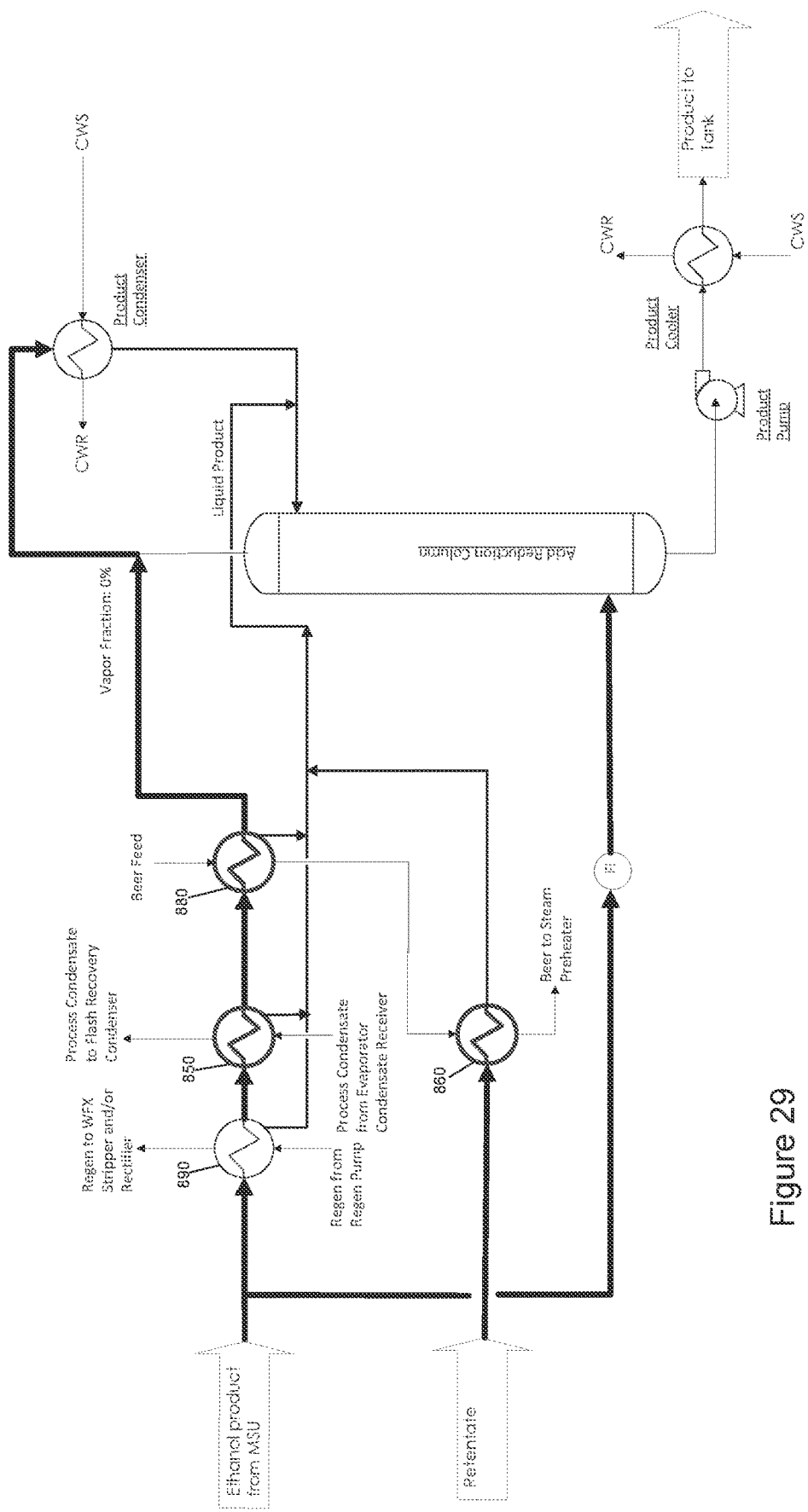
FIG. 29 is a schematic illustration of yet another non-limiting example embodiment of a system for heat integration in ethanol production according to the present disclosure.

Referring to FIG. 29, the illustrated embodiment employs much of the same structure as the embodiment described above in connection with FIG. 26, except that in this embodiment the existing condensate preheater 840 is replaced with a larger new condensate preheater 850 to get substantially all vapors condensed and maximize the heat recovery. The heat recuperated in the illustrated embodiment is equivalent to up to 1,600 BTU/gal.

Figure 30:
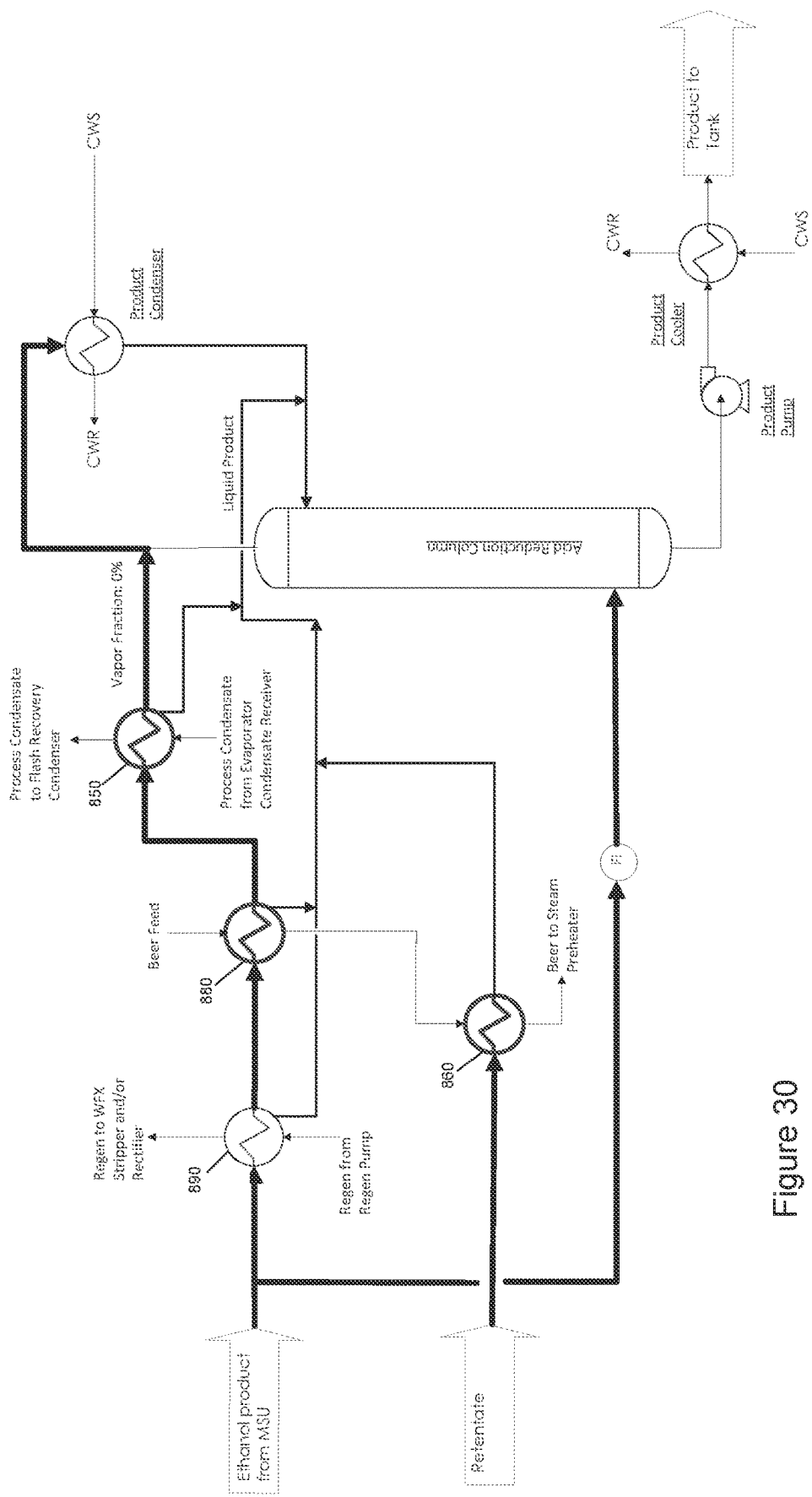
FIG. 30 is a schematic illustration of yet another non-limiting example embodiment of a system for heat integration in ethanol production according to the present disclosure.

Referring to FIG. 30, illustrated embodiment employs much of the same structure as the embodiment described above in connection with FIG. 29, except that in this embodiment the larger new condensate preheater 850 is placed after the beer preheater 880. The heat recuperated in the illustrated embodiment is equivalent to up to 1,600 BTU/gal.

Figure 31:
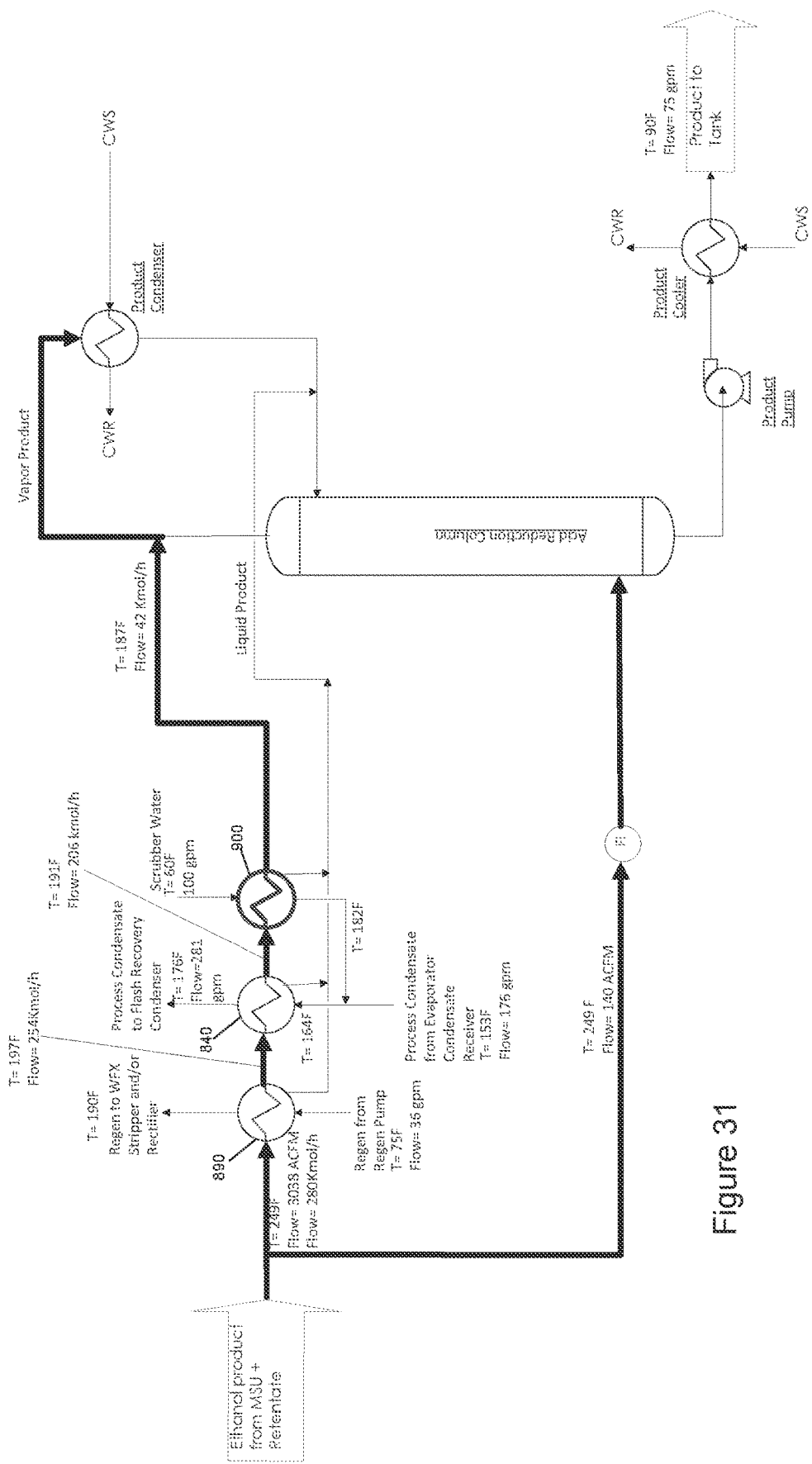
FIG. 31 is a schematic illustration of yet another non-limiting example embodiment of a system for heat integration in ethanol production according to the present disclosure.
Figure 32:
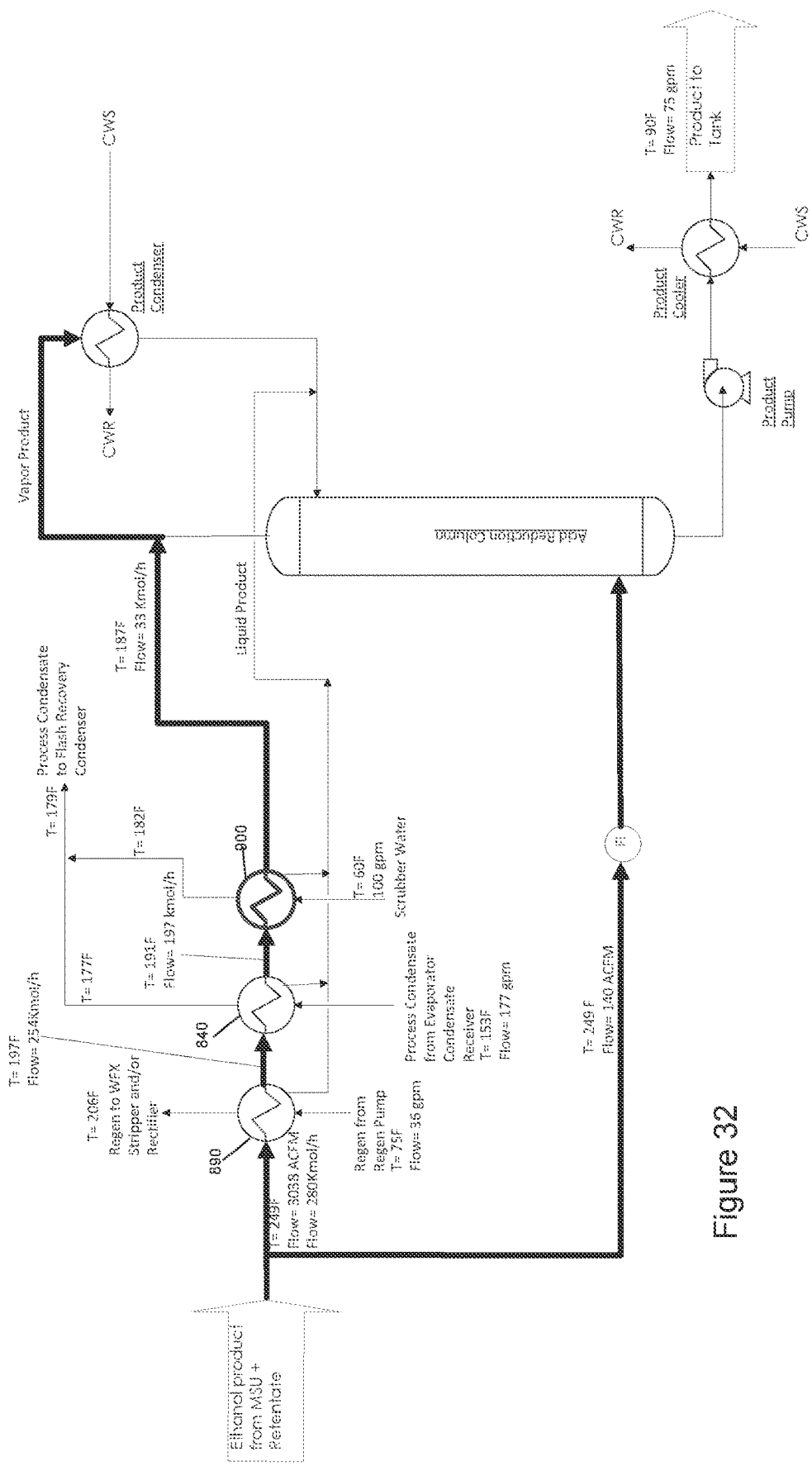
FIG. 32 is a schematic illustration of yet another non-limiting example embodiment of a system for heat integration in ethanol production according to the present disclosure.
Figure 33:
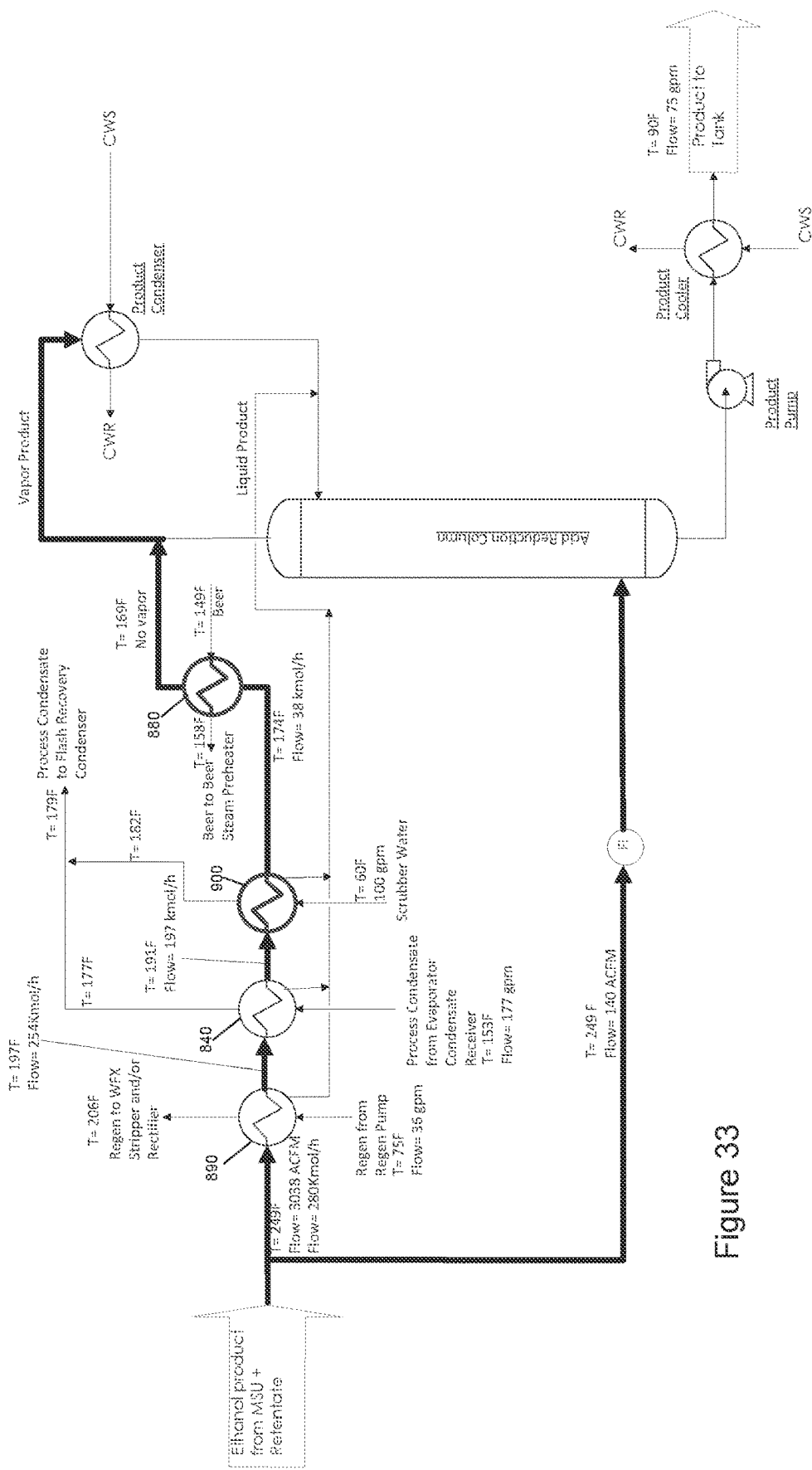
FIG. 33 is a schematic illustration of yet another non-limiting example embodiment of a system for heat integration in ethanol production according to the present disclosure.
Figure 34:
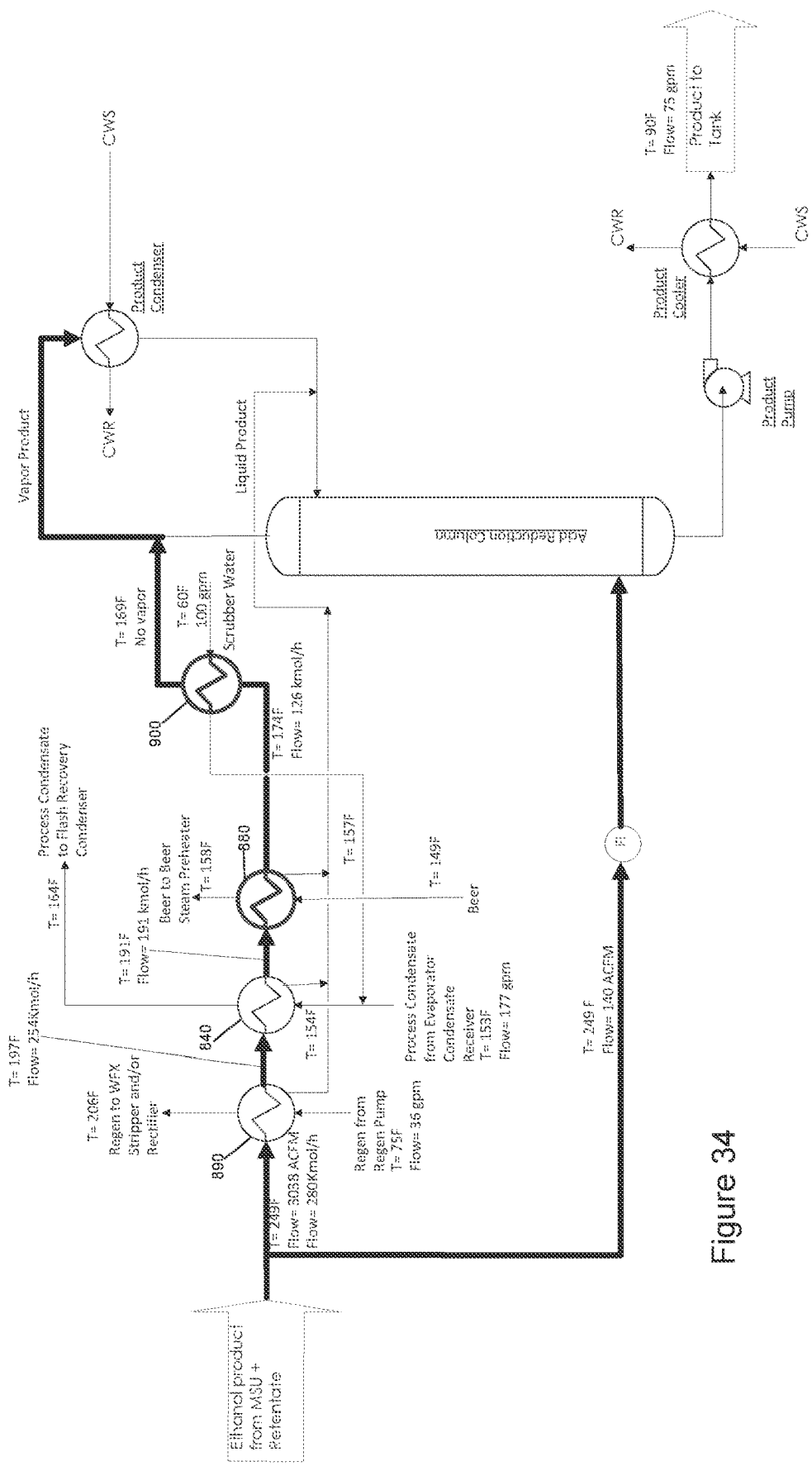
FIG. 34 is a schematic illustration of yet another non-limiting example embodiment of a system for heat integration in ethanol production according to the present disclosure.

FIGS. 31-34 illustrate processes and systems for recovering heat energy according to another embodiment of the invention. Referring to FIG. 31, in the illustrated embodiment a scrubber water preheater 900 is added. The preheated scrubber water is mixed with process condensate before the existing condensate preheater 840. Referring to FIG. 32, in the illustrated embodiment a scrubber water preheater 900 is added, and the preheated scrubber water is mixed with process condensate after the existing condensate preheater 840. Referring to FIG. 33, in the illustrated embodiment a beer preheater 880 is added after the new scrubber water preheater 900. Referring to FIG. 34, illustrated embodiment employs much of the same structure as the embodiment described above in connection with FIG. 33, except that in this embodiment the beer preheater 880 is moved before the new scrubber water preheater 900.

Energy savings for the 4 cases illustrated in FIGS. 31-34, compared with the base case, are presented in Table 2. In particular, the significant magnitude of energy reductions of the embodiment illustrated in FIG. 34, which is adding a beer preheater 880 before a scrubber water preheater 900, was unexpected and surprising.

TABLE 2

|  | FIG. 31 | FIG. 32 | FIG. 33 | FIG. 34 |
|---|---|---|---|---|
| Energy savings, BTU/std gallon product | 750 | 830 | 1140 | 1160 |
| Scrubber water preheater T approach, F. | 9 | 9 | 9 | 17 |
| Beer preheater T approach, F. | N/A | N/A | 16 | 27 |

Figure 35:
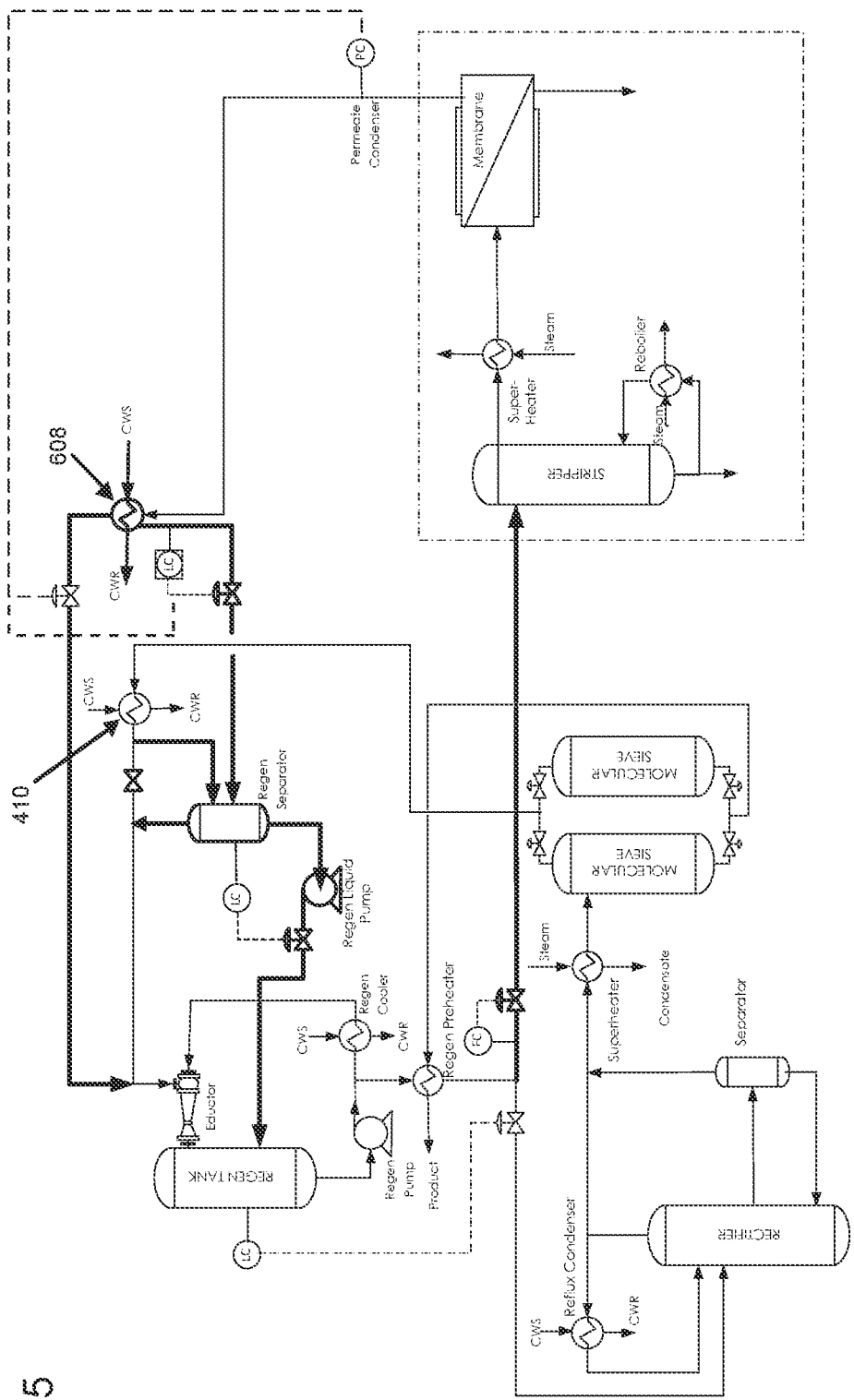
FIG. 35 is a schematic illustration of yet another non-limiting example embodiment of a system for heat integration in ethanol production according to the present disclosure.
Figure 36:
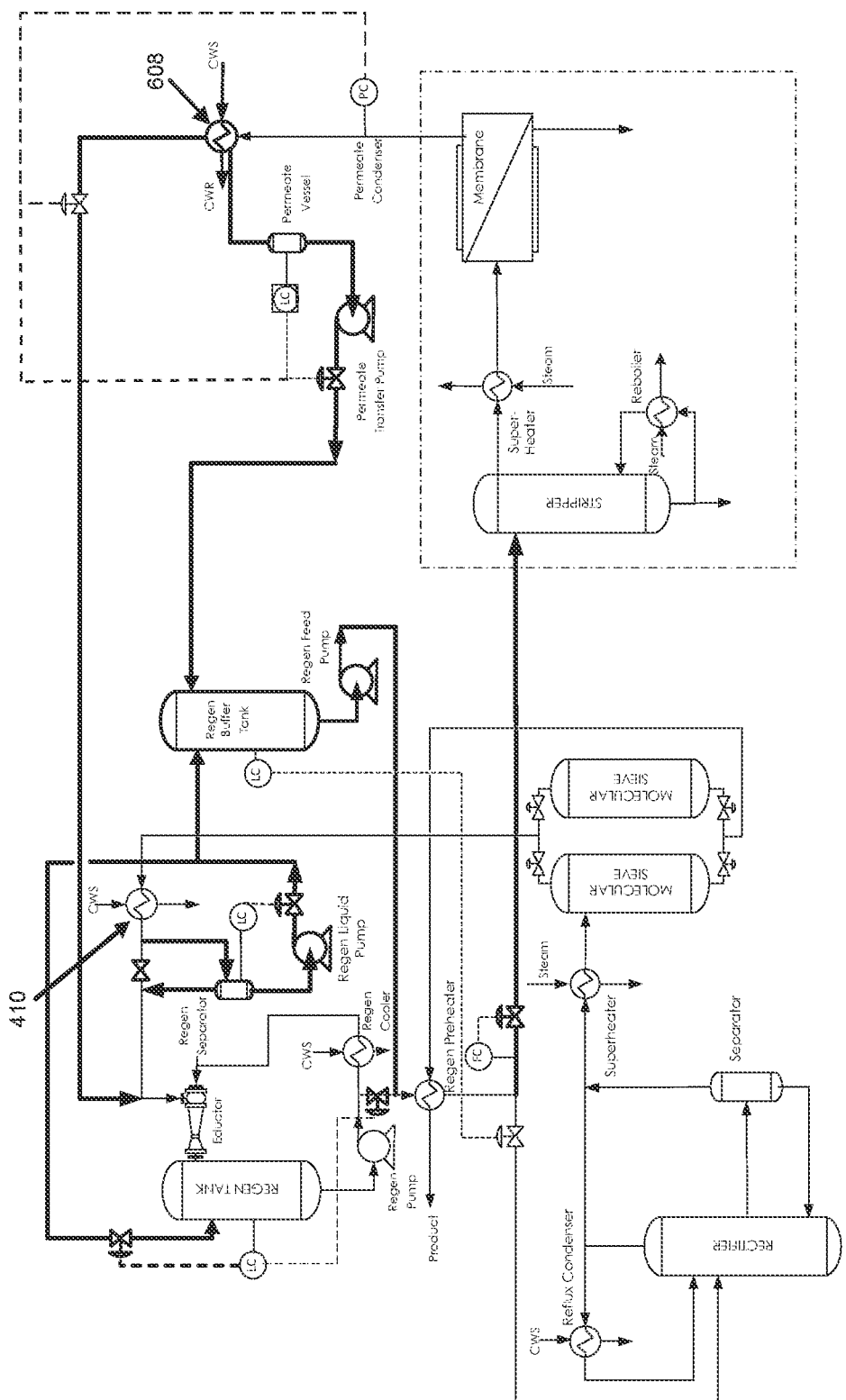
FIG. 36 is a schematic illustration of yet another non-limiting example embodiment of a system for heat integration in ethanol production according to the present disclosure.

FIGS. 35-36 illustrate processes and systems for recovering heat energy according to another embodiment of the invention. In some prior systems, the condensed liquid regen and the incondensable gases/vapor from the regenerate condensation/vacuum system 410 are pulled to the suction side of the eductor. The motive fluid of the eductor is fed from the regen pump through a regen cooler. Liquid regen and incondensable gases/vapor are discharged from the eductor to the regen tank and separated in the regen tank. In this vacuum configuration, power consumed by the regeneration pump is significant due to drawing the liquid regen from the regen condenser to the suction nozzle of the eductor. A benefit of the processes and systems according to the illustrated embodiments is to save pump power by drawing only the incondensable gases/vapor to the suction side of the eductor while the liquid regen is discharged to the regen tank by a pump.

Referring to FIG. 35, in the illustrated embodiment the liquid permeate from the permeate condenser is drained to the regen separator by gravity, and the incondensable gases/vapor from the permeate condenser are tied in to the eductor suction line. A control valve may be needed on the permeate liquid line to maintain a liquid permeate level, and to help the vacuum buildup in permeate condenser during start-up. A control valve may be required on the permeate vapor line to control the vacuum during start-up and normal operation.

Referring to FIG. 36, in the illustrated embodiment a regen buffer tank and a regen feed pump are added to allow more flexible operation on the membrane system. If permeate gravity drain to the regen separator is impossible, then a permeate vessel and a permeate transfer pump may be required to send the permeate liquid to the regen buffer tank. In certain non-limiting embodiments, a control loop may be added for the permeate pressure control. Depending on the usage requirements or preferences for the particular plant, adjusting only the control valve on the permeate vapor may not provide the requisite permeate pressure. Without wishing to be bound to any particular theory, it is believed that in certain embodiments all vapors may be condensed in the permeate condenser and insufficient incondensable gases may be contained in the permeate vapor. In these embodiments, the liquid level may be used to control the permeate pressure during shutdown. When the permeate liquid level is building up in the permeate condenser, the heat transfer area may be reduced, and the permeate pressure may be increased.

Although FIGS. 1-36 illustrate example systems and methods to be used in combination with a separation system 130, it is contemplated that heat and power savings can be achieved by implementing a variety of systems and methods which can be installed separately or in combination including, without being limited to i) a separation system (FIGS. 1-5 and 7), ii) a depressure recovery system (FIG. 6), iii) a heat exchanger network prior to the acid reduction column (FIGS. 9-34), and iv) a regenerate condensation vacuum system (FIGS. 35-36).

Although the foregoing description has necessarily presented only a limited number of embodiments, those of ordinary skill in the relevant art will appreciate that various changes in the processes and systems other details of the examples that have been described and illustrated herein may be made by those skilled in the art, and all such modifications will remain within the principle and scope of the present disclosure as expressed herein and in the appended claims. The present inventions are intended to cover modifications that are within the principle and scope of the inventions, as defined by the claims. It will also be appreciated by those skilled in the art that changes could be made to the embodiments above without departing from the broad inventive concept thereof.

In the present description of non-limiting embodiments and in the claims, other than in in the operating examples or where otherwise indicated, all numbers expressing quantities or characteristics of ingredients and products, processing conditions, and the like are to be understood as being modified in all instances by the term "about." Accordingly, unless indicated to the contrary, any numerical parameters set forth in the following description and the attached claims are approximations that may vary depending upon the desired properties one seeks to obtain in the processes and systems according to the present disclosure. At the very least, and not as an attempt to limit the application of the doctrine of equivalents to the scope of the claims, each numerical parameter should at least be construed in light of the number of reported significant digits and by applying ordinary rounding techniques. Further, as used herein phrases such as "at least a portion" with reference to a stream mean any portion of the referenced stream or all of the referenced stream.

We claim:

1. A system for heat integration in ethanol production, the system comprising:
one or more distillation units each configured to receive a feed mixture including ethanol and water, to remove at least a portion of the water, and to form a vaporous overhead stream;
a first heat exchanger, configured to receive the vaporous overhead stream to exchange heat against a first cold stream to output the vaporous overhead stream as a first cooled vapor stream having a lower temperature and a lower vapor fraction than the vaporous overhead stream; and
a second heat exchanger, configured to receive the first cooled vapor stream to exchange heat against a second cold stream to output a second cooled vapor stream having a lower temperature and a lower vapor fraction than the first cooled vapor stream; and
a plurality of molecular sieve units configured to contact the second cooled vapor stream the plurality of molecular sieve units configured to form a product stream and one or more regenerate streams, and the plurality of molecular sieve units configured to be regenerated by vacuum and optionally a portion of the product stream to form one or more regenerate streams;
a feed tank configured to receive at least one selected from the group consisting of a condensed portion of the regenerate streams and a portion of a vaporous depressure stream, to form a feed stream; and
a separation system configured to contact the feed stream, thereby forming a permeate, a retentate, and a stripper bottom stream.

2. The system of claim 1, wherein the feed tank comprises a heat recovery unit configured to receive at least a portion of the depressure stream and at least one selected from at least a portion of scrubber water streams, at least a portion of a fusel oil stream produced by the one or more distillation units, at least the condensed portion of the regenerate streams, and at least a portion of the permeate, whereby heat is exchanged therebetween.

3. The system of claim 1, further comprising:
an acid reduction column, configured to receive a liquid product stream.

4. The system of claim 3, wherein the vaporous overhead stream provided to the first heat exchanger is a first portion of an ethanol product output by the system, and a second portion of the ethanol product output by the system is provided directly to the acid reduction column.

5. The system of claim 3, wherein the second heat exchanger includes a primary heat exchanger, a secondary heat exchanger, and a tertiary heat exchanger, wherein:
the primary heat exchanger receives the first cooled vapor stream from the first heat exchanger and the second cold stream from the tertiary heat exchanger to exchange heat against the first cooled vapor stream to produce a first intermediate vapor stream having a temperature between the temperatures of the first cooled vapor stream and the second cooled vapor stream and a vapor fraction between the vapor fractions of the first cooled vapor stream and the second cooled vapor stream;
the secondary heat exchanger receives the first intermediate vapor stream from the primary heat exchanger and a third cold stream to exchange heat against the first intermediate vapor stream to produce a second intermediate vapor stream and direct a vaporized portion of the third cold stream to the acid reduction column after exchanging heat with the first intermediate vapor stream, the second intermediate vapor stream having a temperature between the temperatures of the first intermediate vapor stream and the second cooled vapor stream and a vapor fraction between the vapor fractions of the first intermediate vapor stream and the second cooled vapor stream; and the tertiary heat exchanger receives the second intermediate vapor stream and the second cold stream to exchange heat against the second intermediate vapor stream to produce the second cooled vapor stream and directs the second cold stream to the primary heat exchanger.

6. The system of claim 1, further comprising:
a condenser, configured to produce a liquid product stream from the second cooled vapor stream.

7. The system of claim 6, wherein the first heat exchanger produces the first cooled vapor stream and a first portion of the liquid product stream, the second heat exchanger produces the second cooled vapor stream and a second portion of the liquid product stream, and the condenser produces a remainder of the liquid product stream.

8. The system of claim 6, further comprising:
a third heat exchanger disposed between the second heat exchanger and the condenser, configured to receive the second cooled vapor stream to exchange heat against a third cold stream to cool the second cooled vapor stream for provision to the condenser;
wherein the second heat exchanger includes a primary heat exchanger and a secondary heat exchanger, wherein the primary heat exchanger receives the first cooled vapor stream and the second cold stream to output an intermediate cooled vapor stream having a temperature between the temperatures of the first cooled vapor stream and the second cooled vapor stream and a vapor fraction between the vapor fractions of the first cooled vapor stream and the second cooled vapor stream, and wherein the secondary heat exchanger receives the intermediate cooled vapor stream and the second cold stream from the primary heat exchanger to output the second cooled vapor stream and the second cold stream.

9. The system of claim 6, further comprising:
a third heat exchanger disposed between the second heat exchanger and the condenser, configured to receive the second cooled vapor stream to exchange heat against a third cold stream to cool the second cooled vapor stream for provision to the condenser;
wherein the second heat exchanger includes a primary heat exchanger and a secondary heat exchanger, wherein the primary heat exchanger receives the first cooled vapor stream from the first heat exchanger and the second cold stream from the secondary heat exchanger to output an intermediate cooled vapor stream; and
wherein the secondary heat exchanger receives the intermediate cooled vapor stream and the second cold stream to output the second cooled vapor stream to the third heat exchanger and the second cold stream to the primary heat exchanger.

10. The system of claim 6, further comprising:
a third heat exchanger disposed between the second heat exchanger and the condenser, configured to receive the second cooled vapor stream and a third cold stream to cool the second cooled vapor stream for provision to the condenser and to direct the third cold stream to the second heat exchanger as the second cold stream after exchanging heat against the second cooled vapor stream;
wherein the second heat exchanger includes a primary heat exchanger and a secondary heat exchanger;
wherein the primary heat exchanger receives the first cooled vapor stream from the first heat exchanger and a second cold stream including the third cold stream from the third heat exchanger to output an intermediate cooled vapor stream; and
wherein the secondary heat exchanger receives the intermediate cooled vapor stream and a fourth cold stream to output the second cooled vapor stream and the fourth cold stream.

11. The system of claim 1, wherein:
the second heat exchanger includes a primary heat exchanger and a secondary heat exchanger,
the primary heat exchanger receives the first cooled vapor stream from the first heat exchanger and the second cold stream to output an intermediate cooled vapor stream to the secondary heat exchanger; and
the secondary heat exchanger receives the intermediate cooled vapor stream from the primary heat exchanger and a third cold stream to output the second cooled vapor stream.

12. The system of claim 1, including a molecular sieve unit that directs a first portion of a product stream to the vaporous overhead stream and a second portion to a third heat exchanger to exchange heat with a third cold stream.

13. The system of claim 1, including a membrane that directs a first portion of a retentate stream to the vaporous overhead stream and a second portion to a third heat exchanger to exchange heat with a third cold stream.

14. The system of claim 1, wherein the first heat exchanger and the second heat exchanger are included in a network of heat exchangers that comprises a one or more additional heat exchangers configured to receive the vaporous overhead stream.

15. A system for heat integration in ethanol production, the system comprising:
one or more distillation units that are configured to receive a feed mixture including ethanol and water and to remove at least a first portion of the water from the feed mixture to produce a distillation output;
a plurality of molecular sieves units that are configured to remove a second portion of the water from the distillation output from the one or more distillation units and to output an ethanol product vapor stream;
a first heat exchanger, configured to receive the ethanol product vapor stream to exchange heat against a first cold stream to output the ethanol product vapor stream as a first cooled vapor stream having a lower temperature and a lower vapor fraction than the ethanol product vapor stream; and
a second heat exchanger, configured to receive the first cooled vapor stream to exchange heat against a second cold stream to output a second cooled vapor stream having a lower temperature and a lower vapor fraction than the first cooled vapor stream.

* * * * *